United States Patent [19]

Wenzhi

[11] Patent Number: 5,589,069
[45] Date of Patent: Dec. 31, 1996

[54] METHOD FOR SEPARATING AND ANALYZING IONS BY ELECTROSTATIC ION CHROMATOGRAPHY AND A ZWITTERIONIC STATIONARY PHASE FOR ION CHROMATOGRAPHY AND METHOD FOR SEPARATING AND ANALYZING ANALYTES BY MULTIFUNCTIONAL LIQUID CHROMATOGRAPHY

[75] Inventor: Hu Wenzhi, Nagoya, Japan

[73] Assignee: Soichi Inoue, Japan

[21] Appl. No.: 661,892

[22] Filed: Jun. 12, 1996

Related U.S. Application Data

[63] Continuation of Ser. No. 107,608, Aug. 18, 1993, abandoned.

[30] Foreign Application Priority Data

Oct. 5, 1992 [JP] Japan .................................. 4-290739
Apr. 5, 1993 [JP] Japan .................................. 5-103625

[51] Int. Cl.$^6$ .................................................. B01D 15/08
[52] U.S. Cl. ........................... 210/635; 210/656; 436/161
[58] Field of Search ...................... 210/635, 656, 210/659, 198.2; 436/161

[56] References Cited

U.S. PATENT DOCUMENTS

| | | | |
|---|---|---|---|
| 4,126,574 | 11/1978 | Reinwald | 210/198.2 |
| 4,500,431 | 2/1985 | Miyanaga | 210/198.2 |
| 4,517,241 | 5/1985 | Alpert | 210/659 |
| 4,551,288 | 11/1985 | Kelly | 210/198.2 |
| 4,577,013 | 3/1986 | Merz | 210/656 |
| 4,664,806 | 5/1987 | Merz | 210/198.2 |
| 4,672,042 | 6/1987 | Ross | 210/198.2 |
| 4,726,930 | 2/1988 | Matsushita | 210/198.2 |
| 4,732,686 | 3/1988 | Small | 210/198.2 |
| 4,925,567 | 5/1990 | McAleese | 210/198.2 |
| 5,030,352 | 7/1991 | Varady | 210/198.2 |
| 5,045,190 | 9/1991 | Carbonell | 210/198.2 |
| 5,132,018 | 7/1992 | Jones | 210/198.2 |
| 5,167,827 | 12/1992 | Glatz | 210/198.2 |
| 5,240,602 | 8/1993 | Hammen | 210/198.2 |
| 5,484,733 | 1/1996 | Wenzhi | 436/161 |

FOREIGN PATENT DOCUMENTS 4-110657  4/1992  Japan .................................. 210/198.2

OTHER PUBLICATIONS

The Merck Index, Eleventh Edition, 1989, Merck & Co, Rahway, N.J, p. 313.

"Novel Ion Exchange Chromatographic Method Using Conductimetric Detection", Hamish Small et al., Analytical Chemistry 47(11):1801–1809 (1975).

"Determination of Nitrite in Drinking Water and Environmental Samples by Ion Exclusion Chromatography with Electrochemical Detection", Kim et al., Anal. Chem. 61:1485–1489 (1989).

(List continued on next page.)

*Primary Examiner*—Ernest G. Therkorn
*Attorney, Agent, or Firm*—Finnegan, Henderson, Farabow, Garrett & Dunner, L.L.P.

[57] ABSTRACT

The present invention relates to a method for separating and analyzing ions by electrostatic ion chromatography using water as the eluent not only for the analysis of the group of anions or cations but also for the simultaneous and simple analysis of the two groups of analyte ions. A solid phase packed in a separation column to be used therefor is a zwitterionic stationary phase, comprising a support carrier and a zwitterionic layer formed by directly or indirectly coating or immobilized a compound having both of a positive-charge portion and a negative-charge portion (an ammonium salt or amide portion, and a sulfonate ion portion or carboxylate ion portion) on the surface of the support carrier for detecting given separated ions by ultraviolet method etc. And another present invention relates to a method for separating and analyzing inorganic and organic components etc. simultaneously by multi-functional liquid chromatography.

12 Claims, 36 Drawing Sheets

OTHER PUBLICATIONS

"Determination of Nitrite and Nitrate in Water and Food Samples by Ion Interaction Chromatography", Iskandarani et al., Anal. Chem. 54:2601–2603 (1982).

"Liquid Chromatographic Separation and Indirect Detection of Inorganic Anions Using Iron(II) 1, 10–Phenanthroline as a Mobile Phase Additive", Rigas, et al., Anal. Chem. 58:2226–2233 (1986).

"Micelle Exclusion Chromatography of Inorganic Anions", Tetsuo Okada, Anal. Chem. 60:1511–1516 (1988).

"Isotachophoresis", J. L. Beckers et al., J. Chromatog., 51:339–342 (1970).

R=H    NaTDC
R=OH   NaTC

Zwittergent 3-14

(indirect detection method)

(indirect detection method)

METHOD FOR SEPARATING AND ANALYZING IONS BY ELECTROSTATIC ION CHROMATOGRAPHY AND A ZWITTERIONIC STATIONARY PHASE FOR ION CHROMATOGRAPHY AND METHOD FOR SEPARATING AND ANALYZING ANALYTES BY MULTIFUNCTIONAL LIQUID CHROMATOGRAPHY

This application is a continuation of application Ser. No. 08/107,608, filed Aug. 18, 1993, now abandoned.

BACKGROUND OF THE INVENTION

1. Field of the Invention

The present invention relates to a method for separating and analyzing ions by electrostatic ion chromatography and a zwitterionic stationary phase for ion chromatography. More specifically, the present invention relates to a method for separating and analyzing analyte ions by using the simultaneous electrostatic repulsion and attraction forces from both of the positive and negative charges of the stationary phase.

The another present invention relates to a method for separating and analyzing analytes by multi-functional liquid chromatography. More specifically, the present invention relates to a method for not only separation of ions but also separation of enantiomers, and rapid separation of large organic compounds such as proteins, moreover simultaneous separation of ions (inorganic cations, inorganic anions, organic ions such as amino acids) and organic compounds such as proteins by using a helical stationary phase where both positive and negative charges possess in a single molecule of the stationary phase.

The present invention is for use in the quantitative and qualitative analysis of ions etc., or in the isolation of separated ions etc., or in diagnosing diseases based on the presence of a peak on a chromatogram which is observed only in a specific patient.

2. Prior Art

As a method for analyzing (separating) components (or ions) to be analyzed, it is known ion chromatography with a stationary phase packed with an ion exchange resin. As such ion chromatography, there have been known ion exchange method (Anal. Chem. 1975, 47, 1801–1809); ion exclusion method (Anal. Chem. 1989, 61, 1485–1489); ion interaction method (Anal. Chem. 1982, 54, 2601–2603; Anal. Chem. 1986, 58, 2226–2233); micelle particle exclusion method (Anal. Chem. 1988, 60, 1511–1516); electrophoresis (J. Chromatog. 51 (1970), 339–342) and a combination of reverse phase chromatography and ion exclusion method (Japanese Patent Laid-open No. 4-110657), and the like.

According to the above types of liquid chromatography, however, the simultaneous separation of inorganic cat ions, anions, and organic compounds can not be achieved using a single stationary phase.

Problems to be Solved by the Invention

According to the above types of ion chromatography, however, a mobile phase (eluent) should contain ions because analyte ions are substituted from an ion exchange column; furthermore, cations and anions cannot be separated simultaneously. The combination of reverse phase-and ion exclusion chromatography has the same drawbacks as those of ion exchange chromatography, further involving the complexity in the combination. Additionally, other types of ion chromatography require specific reagents, while electrophoresis requires the application of a voltage.

And by any of the liquid chromatography of prior art, the simultaneous separation of inorganic cations, anions and organic compounds (amino acids and proteins etc.) can not be achieved, with a single stationary phase.

SUMMARY OF THE INVENTION

Objective of the Invention

By overcoming the above drawbacks, the objective of the present invention is to provide a method for separating and analyzing ions by electrostatic ion chromatography, characterized in that water is used as eluent and that not only either of anionic or cationic analyte ion but also both of the two can be separated and analyzed together. Another objective of the present invention is to provide a zwitterionic stationary phase for use therefor.

The other objective of the present invention is to provide a method for not only separation of ions but also separation of enantiomers, and rapid separation of large organic compounds such as proteins, moreover simultaneous separation of ions (inorganic cations, inorganic anions, organic ions such as amino acids) and organic compounds such as proteins.

The present invention relates to a method for simultaneous separation and characterization of enantiomers, inorganic cations, anions, regular organic compounds and zwitterionic compounds such as amino acids and proteins by a single helical zwitterionic stationary phase liquid chromatography termed "multi-functional liquid chromatography".

Characteristics of the Invention

The present inventor has made various investigations so as to apply the simultaneous electrostatic repulsion and attraction forces from a zwitterionic stationary phase for separation of ions. Thus, the inventor has achieved the present invention.

That is, the method for separating and analyzing ions by the electrostatic chromatography (simply referred to as "the present method for separating and analyzing ions" or as "the presention separation and analysis method", hereinafter) in accordance with the present invention comprises injecting a sample solution containing multiple analyte ions into one end of a packed separation column, thereafter eluting an eluent to separate the analyte ions via the difference in the retention time among the individual analyte ions, wherein a zwitterionic stationary phase is employed, comprising a support carrier and a zwitterionic charged layer formed by directly or indirectly coating a compound having both of a positive-charge portion and a negative-charge portion on the surface of the support carrier. The term "the method for separating and analyzing ions (or "analytes" of another invention)" herein means not only a method comprising separating individual analyte ions etc. and detecting the separated components for analysis but also a method further comprising isolating the individual components.

As described above, the zwitterionic stationary phase for ion chromatography (simply referred to as "zwitterionic stationary phase" hereinbelow) as another aspect of the present invention comprises a support carrier and a zwitterionic layer formed by directly or indirectly coating or immoblized a compound having both of a positive-charge portion and a negative-charge portion on the surface of the support carrier.

Function

Ions are charged particles, so electrostatic repulsion and attraction forces are induced between identically charged ions and between oppositely charged ions, respectively.

The electrostatic stationary phase to he used in the present ion separation and analysis method has a zwitterionic layer formed by coating a compound having both of a positive-charge portion and a negative-charge portion on the surface of the support carrier. When analyte ions are then mobilized with an eluent (mobile phase) to pass through the electrostatic stationary phase, as shown in FIG. 1, the electrostatic repulsion and attraction forces simultaneously occur on the two charged portions of the electrostatic stationary phase. The combination of the electrostatic repulsion and attraction forces (total sum) consequently amounts to what is represented by Formula 1, depending on the number or intensity (degree) of the charges, the radius of hydrated ions and the like.

$$\Delta F = \sum_{i=1}^{n} \left( \epsilon_1 \frac{q(s)^+ q_A{}^n}{r_i^2} - \epsilon_2 \frac{q(s)^- q_A{}^n}{r_i^2} \right) \quad \text{[Formula 1]}$$

In formula 1, n represents the number of charges; $\epsilon_1$ and $\epsilon_2$ represent electrostatic conductivity; $q(s)+$ and $q(s)-$ represent the electron density of negative and positive charges of a zwitterionic stationary phase; $q_A$ represents the electron density of an analyte ion; and r and r' individually represent the electrostatically active distance. The combined electrostatic forces ($\Delta F$) function as newer separation force in the present separation column.

If $\Delta F<0$, electrostatic repulsion force is larger than electrostatic attraction force, and analyte ions cannot be retained in the electrostatic column. On the contrary, analyte ions cannot be eluted from the column, if $\Delta F>\phi$ ($\phi$ represents the transfer force of the mobile phase). If $\Delta F$ satisfies the provision that $\phi \geq \Delta F \geq 0$, the analyte ions can be separated on the column. For example, if $\phi$ (water)$\geq \Delta F \geq 0$, the analyte ions can be separated by the electrostatic column, even using purified water as an eluent. In the same fashion, if $\phi$ (eluent)$\geq \Delta F \geq 0$, the analyte ions can be separated by the column where the eluent is used.

Futhermore, bile micelles are reversed helical aggregates (J. Phys. Chem., *1989, 93, 1536*.), they keep their helical structures even which adsorbed on the ODS stationary phase with hydrophobic interactions (Chromatographia, 1992, 33, 63.). Therefore, the bile micellar coated stationary phase also work as a chiral stationary phase for the separation of isomers.

Effects of the Invention

Not only a solution containing ions but also water can be used as an eluent when the present method is used along with a zwitterionic stationary phase. Therefore the applicable range is wide. And individual ions not only among the group of anions or cations, but also among differently charged ions between anions and cations can be separated well in a simple manner. Thus, the present ion separation and analysis method and the zwitterionic stationary phase are extremely useful. Also, the present invention utilizes an action exhibiting the reverse performance to the performance conventionally known, such that the retention time of analyte anions is prolonged as the increase in the ion concentration in an ionic eluent if employed. Furthermore, a variety of desired ions can be separated and analyzed in simple fashion by appropriately selecting the electrostatic status (negative or positive degree) of a compound having both of a positive-charge portion and a negative-charge portion to form a zwitterionic stationary phase.

Futhermore, when a helical zwitterionic stationary phase is used, separation of inorganic ions, amino acid and proteins etc. can be performed, moreover separation of enatiomer can be performed too. Therfore this chromatography is extremely useful as muliti-functional liquid chromatography.

DETAILED DESCRIPTION OF THE INVENTION

Figure 1:
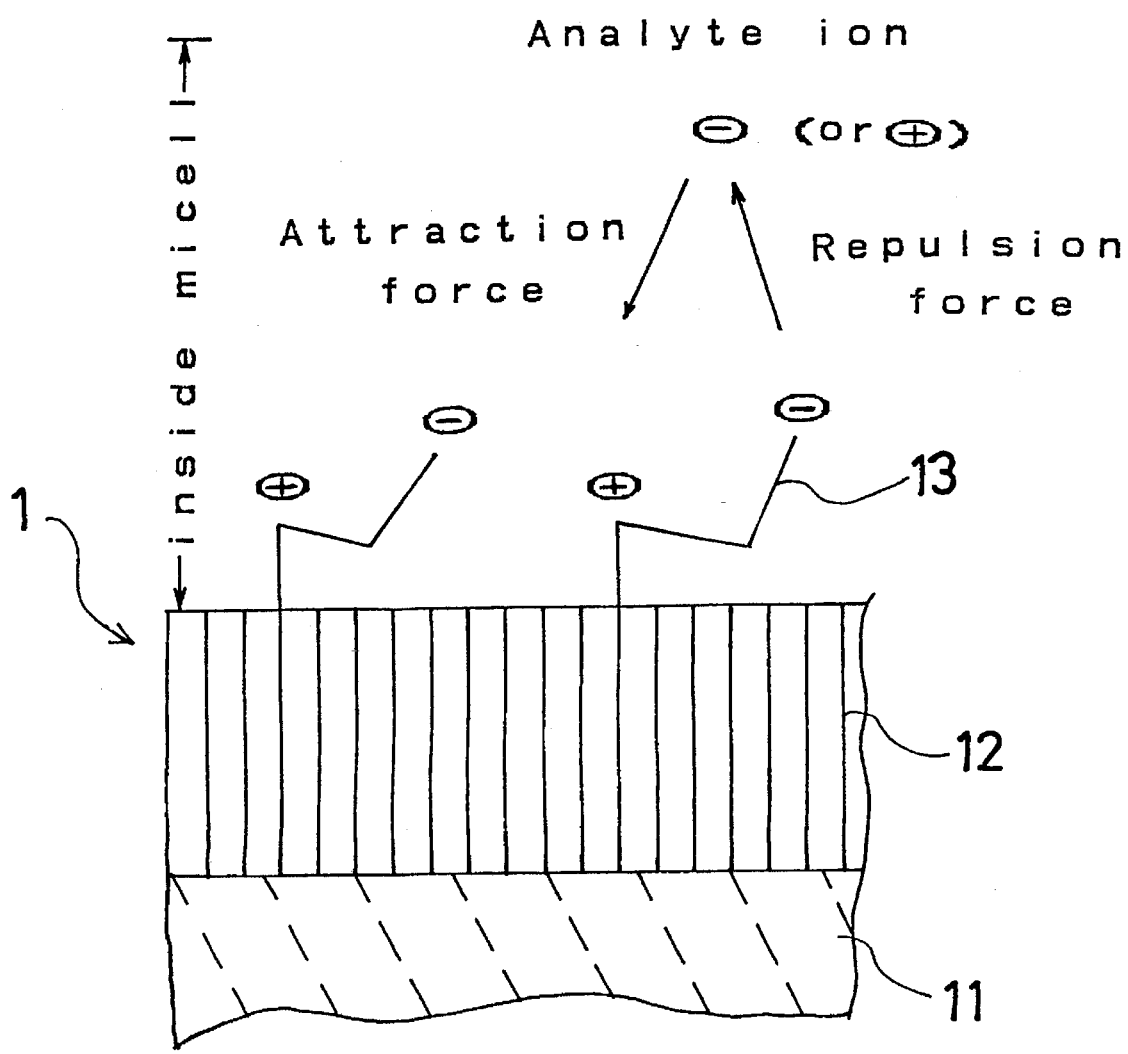
FIG. 1 is a schematic explanatory view of the zwitterionic stationary phase used in Example where analyte ions pass.

In accordance with the present invention, a support carrier of any material, form or size may be used in the aforementioned "zwitterionic stationary phase", without any specific limitation, if a zwitterionic layer can be formed on the surface of the carrier. The material is illustrated, for example, by silica gel, polystyrene and the like, and the surface thereof is preferably porous for ready immobilization. Furthermore, the zwitterionic layer may directly be formed on a carrier to be used, through chemical reaction or physical adsorption; a zwitterionic layer may be formed on the surface of the carrier through a hydrophobic layer being formed thereon as an adhesive layer (in other words, indirectly formed on the surface of the carrier).

For example, a carrier comprises porous silica gel in the aforementioned "zwitterionic stationary phase"; on the surface of the carrier is formed a hydrophobic layer obtained through alkylsilane reaction; and furthermore, the zwitterionic layer is adsorbed and formed onto the surface of the hydrophobic layer. The alkyl group of the alkylsilane is preferably the one with about 12 to 24 carbon atoms so as to provide hydrophobicity; the one with 18 carbon atoms is employed in general.

The aforementioned "compound having both of a positive-charge portion and a negative-charge portion" may be a compound having an ammonium salt portion (cation portion), and a sulfonate ion portion or carboxylate ion portion (anion portion). Furthermore, the compound may be a compound with an amide portion ($\delta^+$ portion), and a sulfonate ion portion or carboxylate ion portion.

More specifically, the latter compound may be illustrated by 3-[3-cholamidepropyl]dimethyl ammonio]-1-propanesulfonate or 3-[3-cholamidepropyl)dimethyl ammonio]-2-hydroxy-1-propanesulfonate or the like; and the former compound may he illustrated by sodium taurodeoxycholate or sodium taurocholate.

The aforementioned "analyte ion" may be selected variously, depending on the objective and use, and may be plural anions only, plural cations only, or a combination of a variety of cations and anions. Furthermore, the valence of these ions is not limited, so a combination of ions with difference valences may also be satisfactory.

The aforementioned "eluent" (also referred to as "mobile phase") may be any one that can transfer a given analyte ion, and may be selected variously, depending on the type of the stationary phase and the species of the analyte ion. As such, inorganic buffer solutions, organic buffer solutions, inorganic solutions or organic solutions may be used, as well as water (purified water, etc.). The ion concentration of the eluent, if it is an ion-containing solution, may be selected variously. In accordance with the present method, the retention time of analyte anions may he prolonged as the increase of the ion concentration in the eluent.

As the "means" for detecting the separated analyte ions, an ultraviolet (referred to as "UV" hereinbelow) detector may be used without limitation; other known means (electric conductivity detector or electrochemical detector) may be used as well.

If the analyte ions to be used with a UV detector contain UV-non-absorptive ions, the eluent therefor may be a solution containing a UV absorbing substance (aqueous solution, organic solution, etc.) (so-called indirect detection method). The term "ion-containing" herein means that only UV-non-absorptive ions are contained or that a combination of UV-absorptive and UV-non-absorptive ions are contained. As such UV-absorptive ionic substance, the salts of water-soluble copper (II) or water-soluble cerium (III) and salicylate may be used for cation and anion analysis, respectively.

Embodiments

The present invention will now be explained in details with reference to examples.

(1) Electrostatic ion chromatography device and conditions therefor

The present device comprises an eluent feeding pump, a separation column connected to the pump, a UV detector for detecting the analyte ions separated through the separation column, a recording device recording the results of the separation, and a sample injector to inject a sample into a connecting tube connected in between the separation column and the pump.

As present system, two liquid chromatography (LC) system shown below were used.

① Micro-LC-system

As such pump, "MF-2 Microfeeder" (manufactured by Azuma Electric Industry, Co. Ltd.) with a 0.5-ml gas-tight injector ("MS-GAN 050" as product name; manufactured by Ito Fuji Corporation) was used. As such sample injecting part, a microvalve ("ML-552" as product name; manufactured by JASCO CO. Ltd.; injection volume, 0.02 μl) was used. As such separation column, there was prepared firstly a column of 150 mm×0.35 mm in internal diameter packed with 5-μm "Develosil ODS-5" (as product name; manufactured by Nomura Chemical; prepared by reacting porous silica gel with octadecyl silane; referred to as ODS carrier).

② Conventional-LC-system

As such pump, "LC-6A" (manufactured by Shimazu Seisakusho Co. Ltd.) was used, as a detector, UV detector or electric conductivity detector was used, and as such column, "LC6A" (manufactured by Kagakuhin-Kensa-Kyokai, a column of 250 mm×4.6 mm in internal diameter) was used, and another condition is the same as aforementioned Micro-LC-system.

As shown in FIG. 1, subsequently, compound 13 (zwitterionic surfactant) having both of a positive-charge portion and a negative-charge portion shown hereinbelow as 1 to 5, was immobilized (or coated) onto the surfaces of the ODS carrier (ODS layer, 12; the carrier thereof, 11) to , prepare zwitterionic stationary phase 1.

Figure 2:
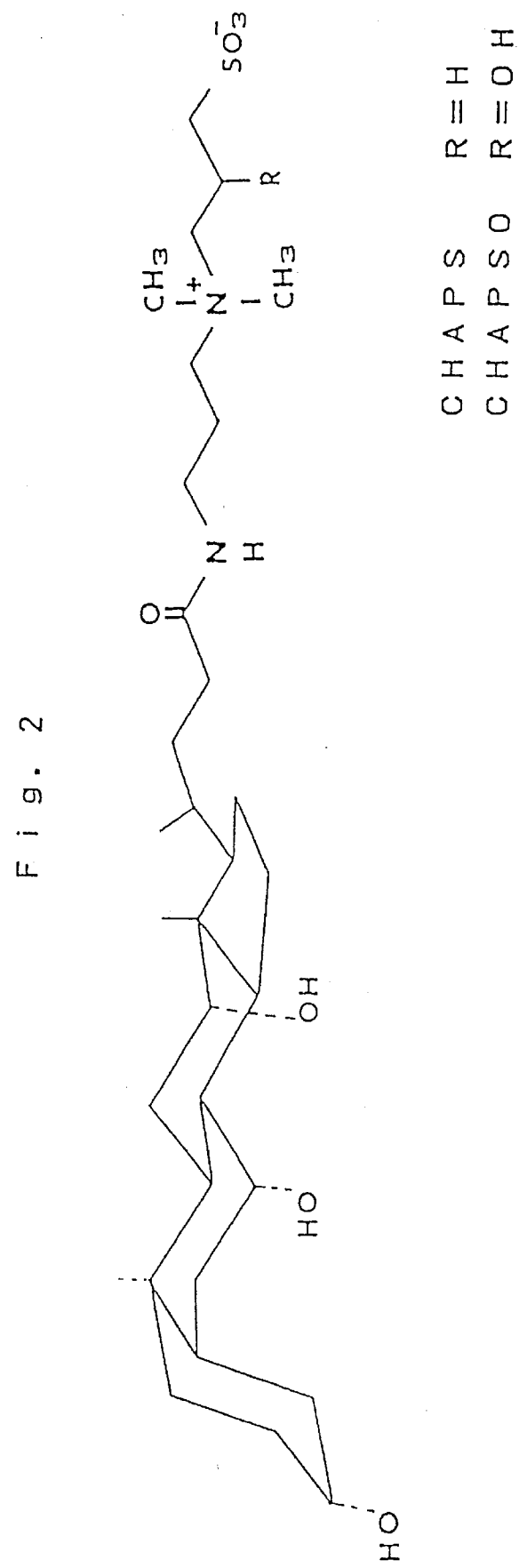
FIG. 2 is an explanatory view depicting the chemical structures of CHAPS and CHAPSO.

1. 3-[(3-Cholamidepropyl)dimethyl ammonio]-1-propanesulfonate (referred to as "CHAPS"; manufactured by Dojin Corporation; depicted in FIG. 2)

2. 3-[(3-Cholamidepropyl)dimethyl ammonio]-2-hydroxy-1-propanesulfonate (referred to as "CHAPSO"; manufactured by Dojin Corporation; depicted in FIG. 2)

Figure 3:
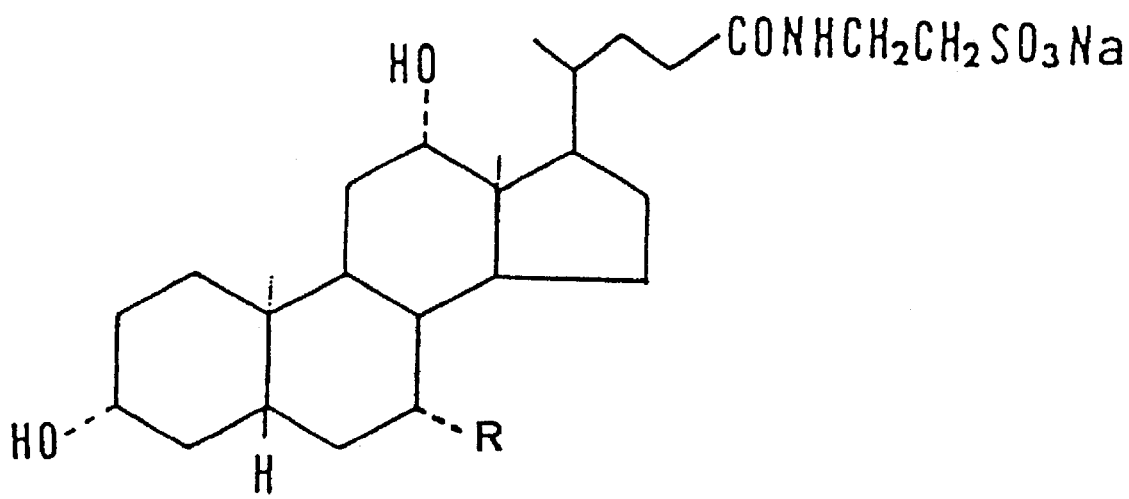
FIG. 3 is an explanatory view depicting the chemical structures each of NaTDC and NaTC.

3. Sodium taurodeoxycholate (referred to as "NaTDC" hereinafter; manufactured by Sigma Corporation, USA; depicted in FIG. 3)

4. Sodium taurocholate (referred to as "NaTC"; manufactured by Sigma Corporation, USA; depicted in FIG. 3)

Figure 4:
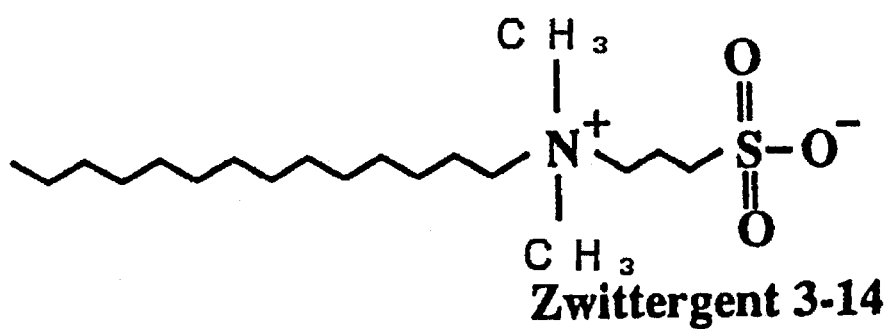
FIG. 4 is an explanatory view depicting the chemical structures of Zwittergent 3-14.

5. [Zwittregent 3–14] [$H_{29}C_{14}N^+$ $(CH_3)_2(CH_2)_3SO_3$, shown in FIG. 4]

The method for immobilization is as follows. An aqueous 30 mmol/liter micellar particle solution (a predetermined surfactant solution) passed through a microcolumn (or conventional-column) packed with the ODS carrier at a flow rate of 2.8 μl/min for 20 to 30 minutes (or 0.7 ml/min for 50 to 60 minutes). Then, the column was washed with purified water at the same flow rate for 30 to 40 minutes. The concentration of the surfactant should he higher than their critical micelle concentration (CMC).

UV detector with a flow cell was used as a detector (detection wave length of 200 to 260 nm); "Chromatopack CR4AX Data Processor" (as product name; manufactured by Shimadzu Seisakusho Corporation) was used as a recording device.

An eluent (mobile phase) flow rate is 2.8 μl/min in the microcolumn and 0.7 ml/min in the conventional-column. And the separation was done at room temperature.

Reagent-grade chemicals manufactured by Wako Chemical Corporation were used, unless otherwise stated. These chemicals were used without further treatment. Purified water was prepared with "Milli-Q System" (as product name; manufactured by Nippon Millipore Corporation) for use.

The analyte ions etc. were selected from the group of inorganic anions only, the group of inorganic cations only, a combined group of inorganic anions and cations, the group of organic ions (amino acid) or α-amylase (protein), depending on the objectives of the following individual experiments. Any inorganic anion or cation may he prepared into the sodium salt or chloride salt, respectively, for use.

With the aforementioned devices under the above conditions, the following experiments were carried out. The conditions were the same as described above, unless otherwise stated.

(2) Separation and analysis of inorganic anions

Figure 5:
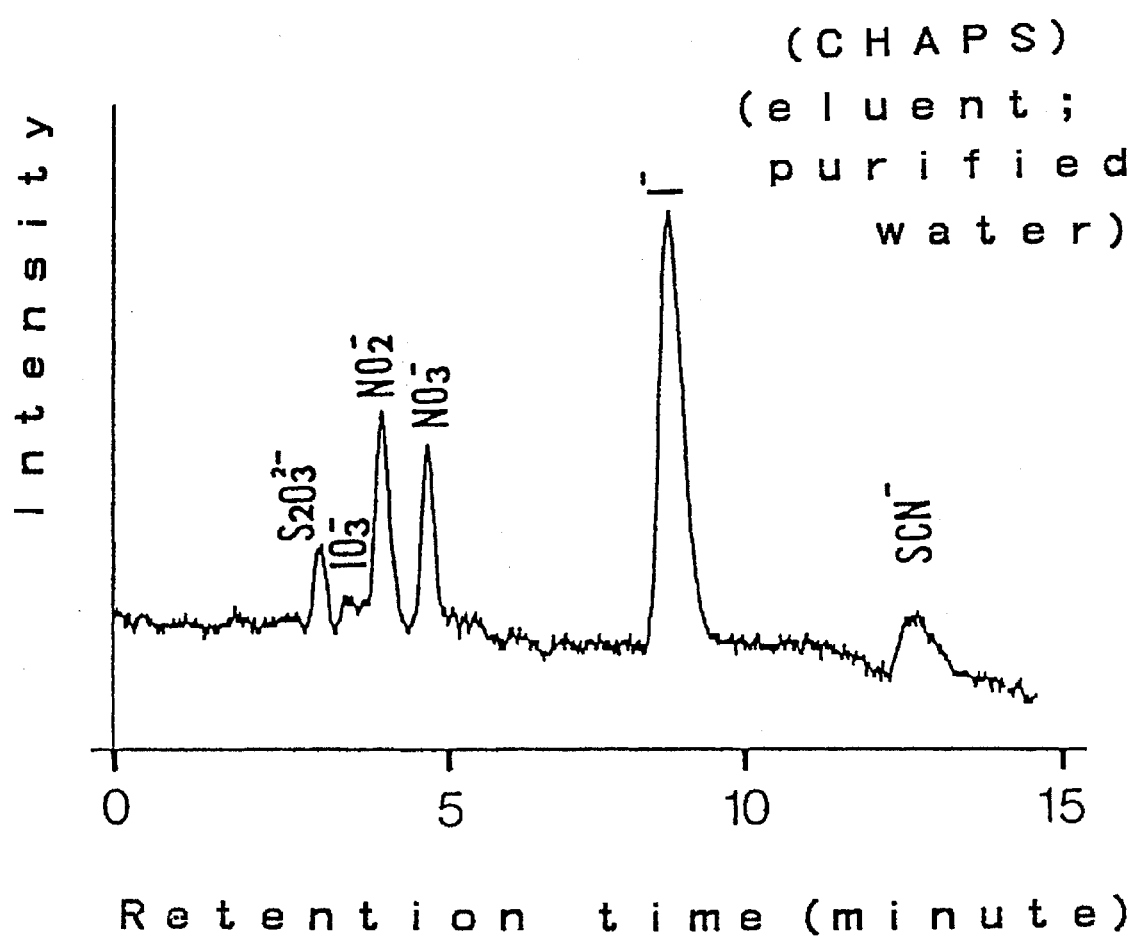
FIG. 5 is an explanatory view depicting the chromatogram from the analysis of six species of UV-absorptive inorganic anions, using CHAPS micellar coated stationary phase and purified water as an eluent in Example.

Under the conditions that the eluent was purified water and the zwitterionic surfactant to be used in the separation column was CHAPS, six species of UV-absorptive inorganic anions ($IO_3^-$, $S_2O_3^{2-}$, $NO_2^-$, $NO_3^-$, $I^-$ and $SCN^-$) were analyzed. The chromatogram is shown in FIG. 5. The results indicate that the six species of the individual ions were excellently separated using purified water as the eluent.

Figure 6:
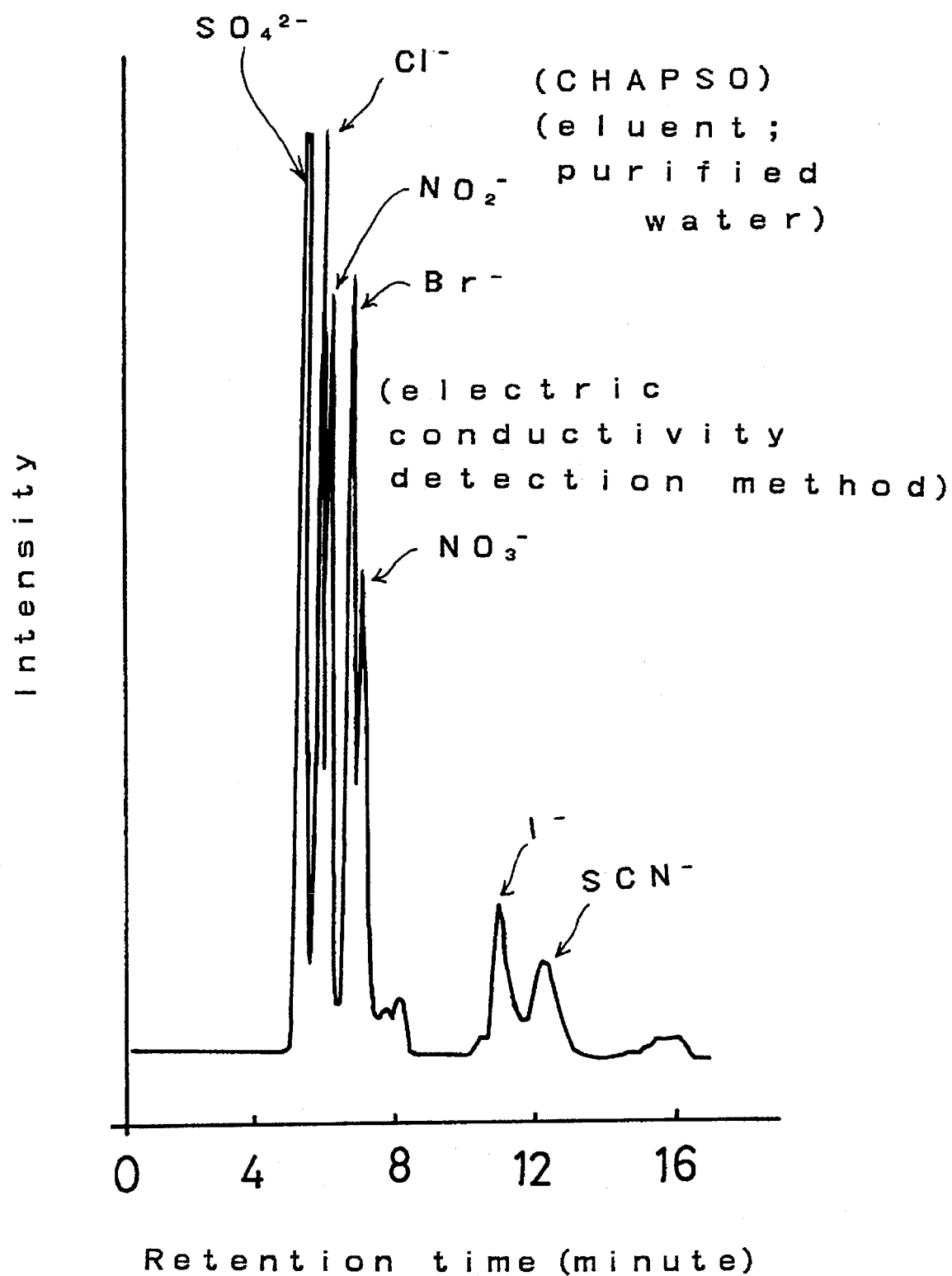
FIG. 6 is an explanatory view depicting the chromatogram from the analysis of seven species of inorganic anions, using CHAPSO micellar coated stationary phase and purified water as an eluent in Example.

Analysis was done by electric conductivity detection method (with an electric conductivity detector; manufactured by Shimadzu Seisakusho Corporation) under the same conditions as those for CHAPS, except that CHAPSO was used in place of CHAPS, as the zwitterionic surfactant to be used in the separation column; purified water and inorganic anions, namely $SO_4^{2-}$, $Cl^-$, $NO_2^-$, $Br^-$, $NO_3^-$, $I^-$, and $SCN^-$, were used as the eluent and analyte ions, respectively. The chromatogram of FIG. 6 was recorded. As shown in the figure, separation was excellent with CHAPSO as in the case of CHAPS.

Figure 7:
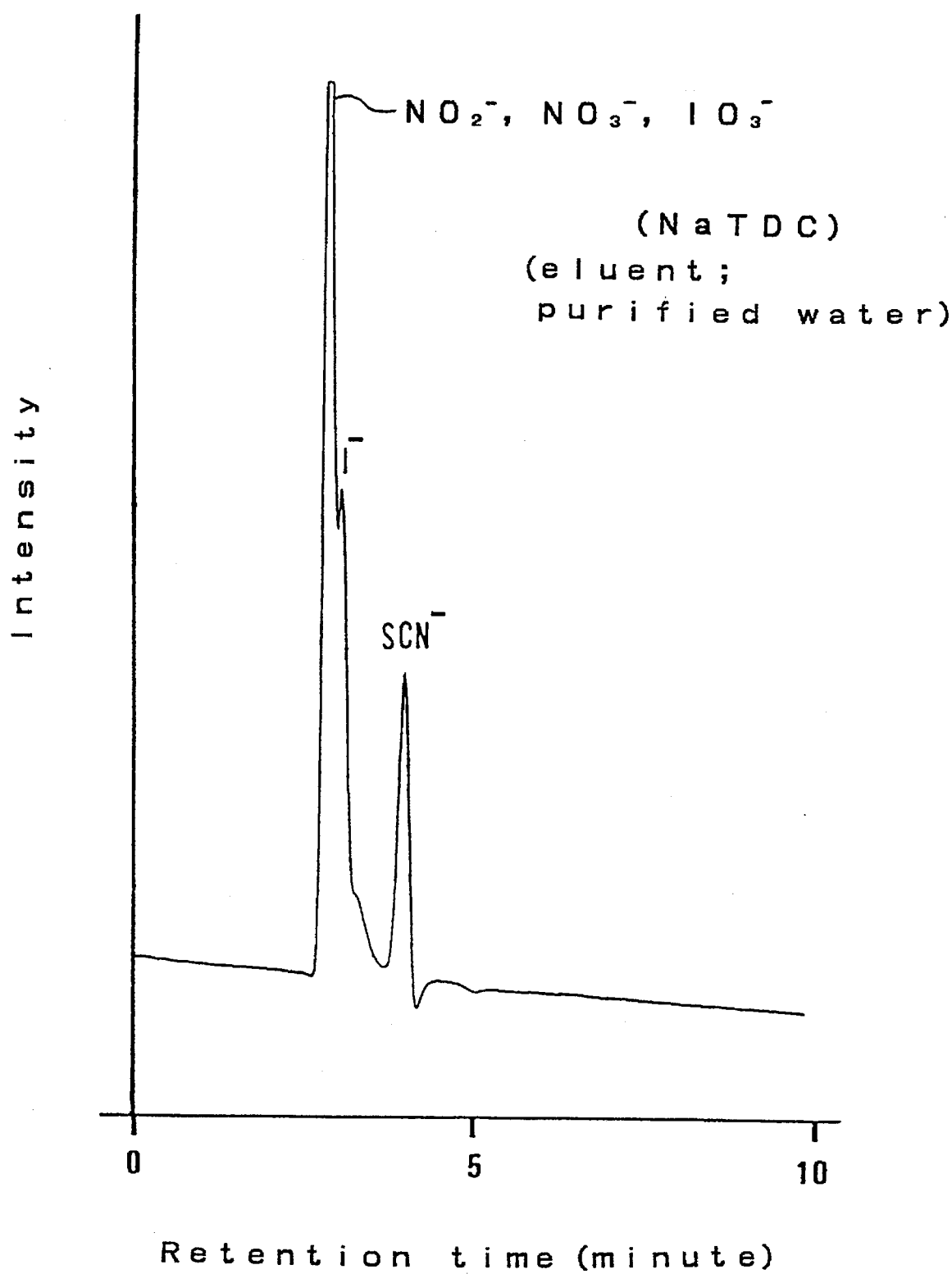
FIG. 7 is an explanatory view of the chromatogram from the analysis of five species of anions using NaTDC micellar coated stationary phase and an eluent, purified water in Example.
Figure 8:
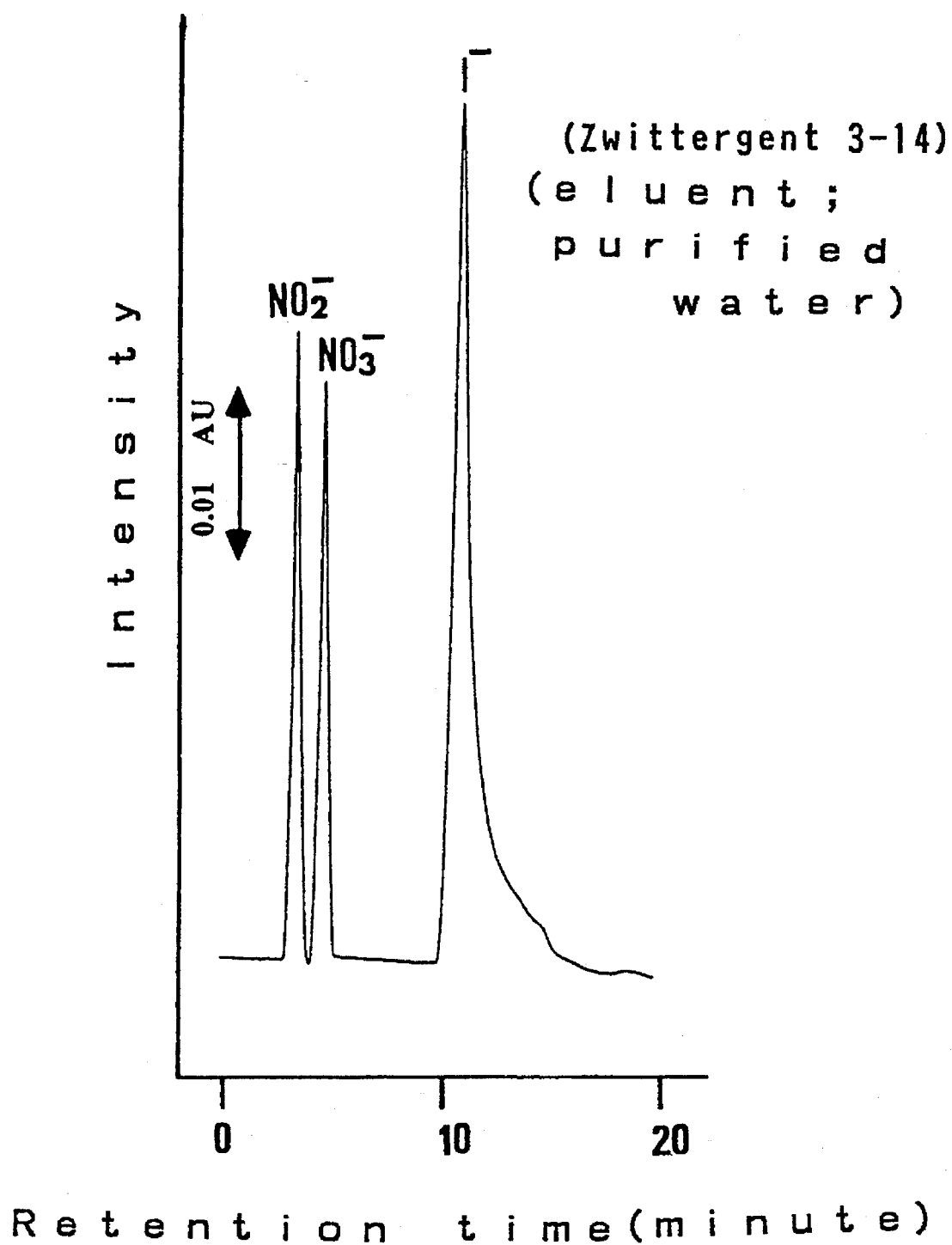
FIG. 8 is an explanatory view of the chromatogram from the analysis of three species of anions using Zwittergent 3-14 stationary phase and an eluent, purified water in Example.

Under the conditions that the eluent was purified water and stationary phase to be used was NaTDC micellar stationary phase with acid treatment, five species of inorganic anions ($I^-$ and $SCN^-$ etc. ) were analyzed in the same way. The chromatogram is shown in FIG. 7. Further, under the conditions that the eluent was purified water and stationary phase to be used was Zwittergent 3-14 solid phase, inorganic anions ($NO_2^-$, $NO_3^-$ and $I^-$) were analyzed. The chromatogram is shown in FIG. 8. And these species were detected by UV-absorption method. These results indicate that separation was excellent with NaTDC stationary phase and Zwittergent 3-14 stationary phase as in the case of CHAPS stationary phase.

(3) Analysis of inorganic cations

Figure 9:
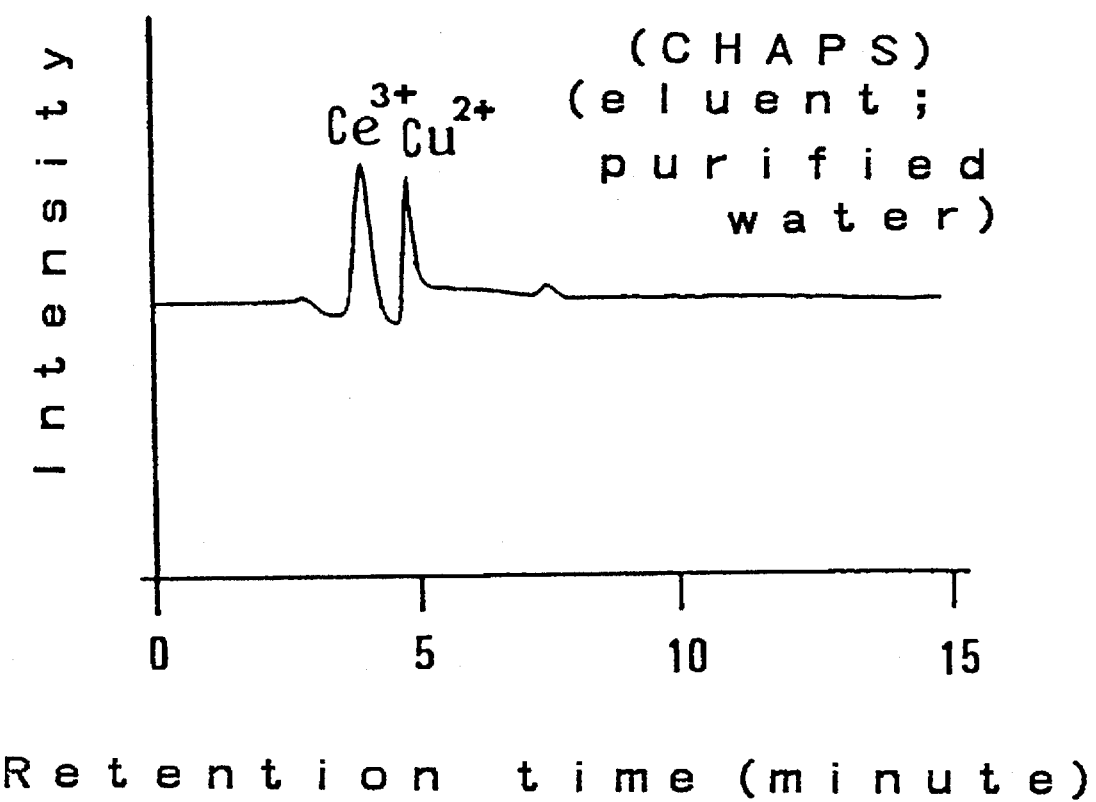
FIG. 9 is an explanatory view depicting the chromatogram from the analysis of two species of UV-absorptive inorganic cations, using CHAPS coated stationary phase and purified water as an eluent in Example.

Under the conditions that the eluent was purified water and the zwitterionic surfactant to be used in the separation column was CHAPS, two species of UV-absorptive inorganic cations ($Ce^{3+}$ and $Cu^{2+}$) were analyzed. The chromatogram is shown in FIG. 9. The results indicate that the two species of the individual cations were excellently separated using water as the eluent.

Figure 10:
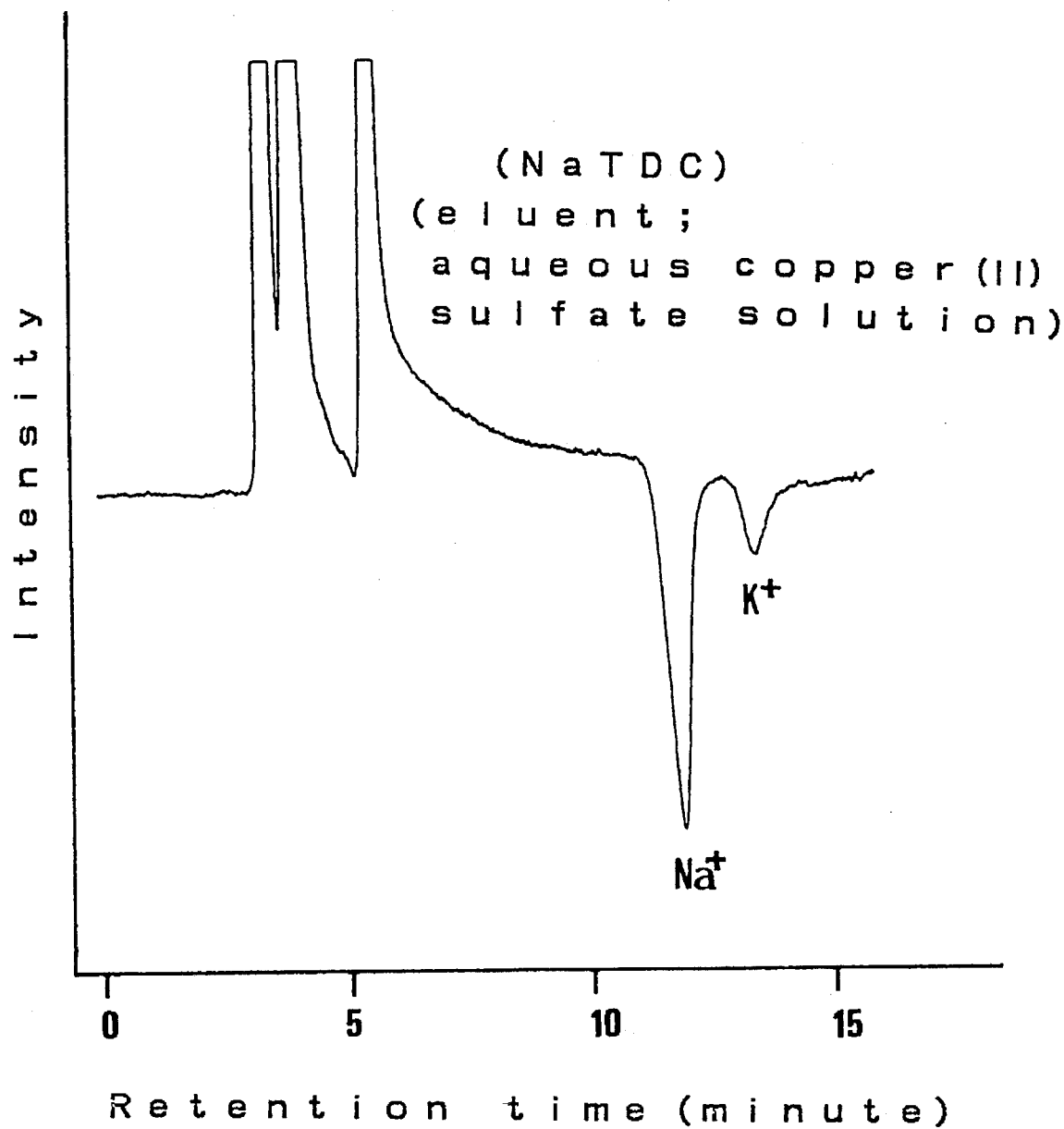
FIG. 10 is an explanatory view of the chromatogram from the analysis of $Na^+$ and $K^+$ using NaTDC micellar coated stationary phase and an eluent, aqueous copper (II) sulfate solution in Example.
Figure 11:
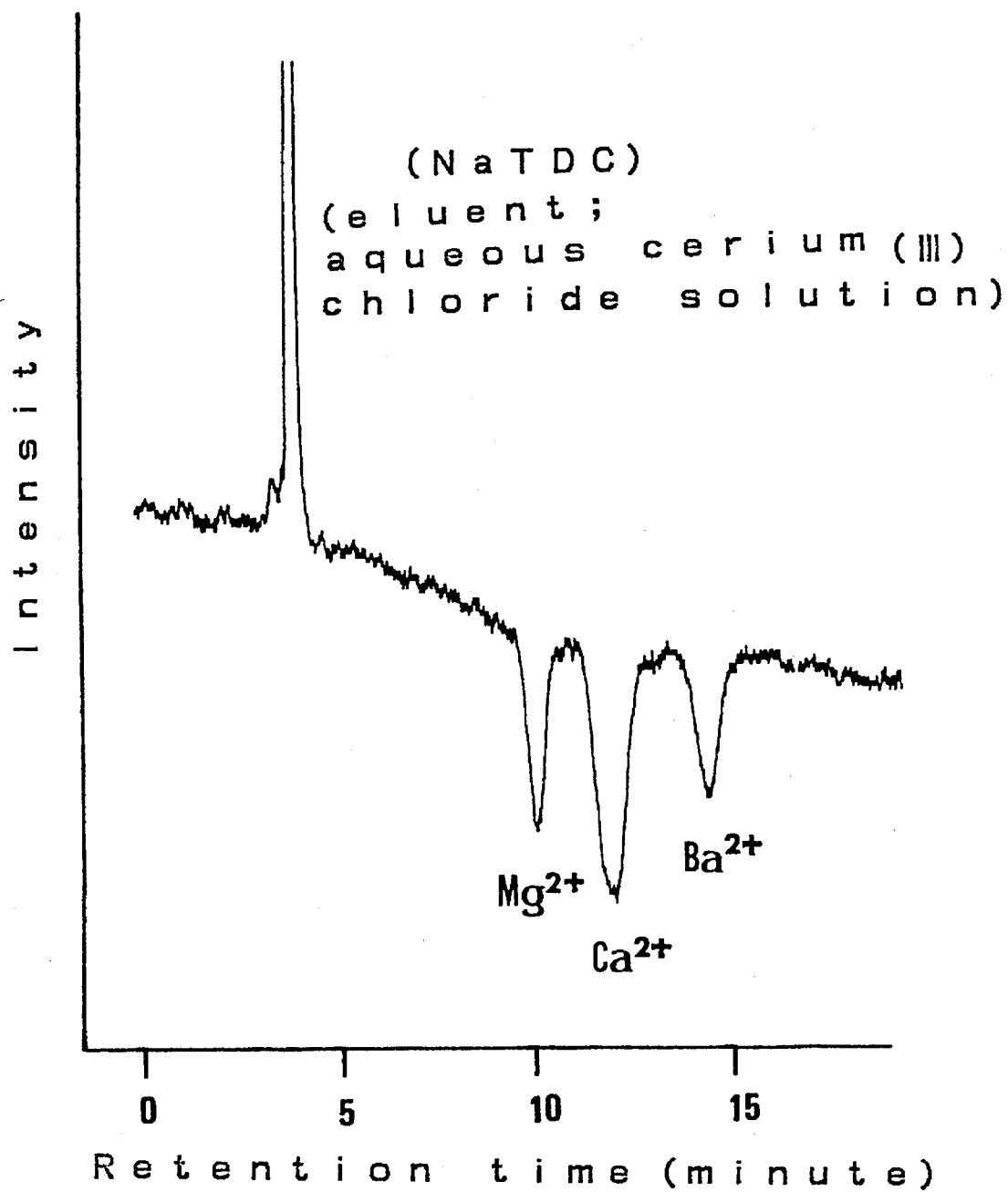
FIG. 11 is an explanatory view of the chromatogram from the analysis of three species of divalent cations using NaTDC micellar coated stationary phase and an eluent, aqueous cerium (III) chloride solution in Example.

Futhermore, under the conditions that the eluent was aqueous copper (II) sulfate solution and the zwitterionic surfactant to be used in the separation column was NaTDC, inorganic cations ($Na^+$ and $K^+$) were analyzed by indirect detection method. The chromatogram is shown in FIG. 10. And under the conditions that the eluent was aqueous cerium (III) chloride solution and the zwitterionic surfactant was NaTDC, divalent inorganic cations ($Mg^{2+}$, $Ca^{2+}$ and $Ba^{2+}$) were analyzed. The chromatogram is shown in FIG. 11. These results indicate that the species of the individual cations were excellently separated using NaTDC stationary phase as in the case of CHAPS stationary phase.

(4) Analysis of zwitterionic organic ions

Figure 12:
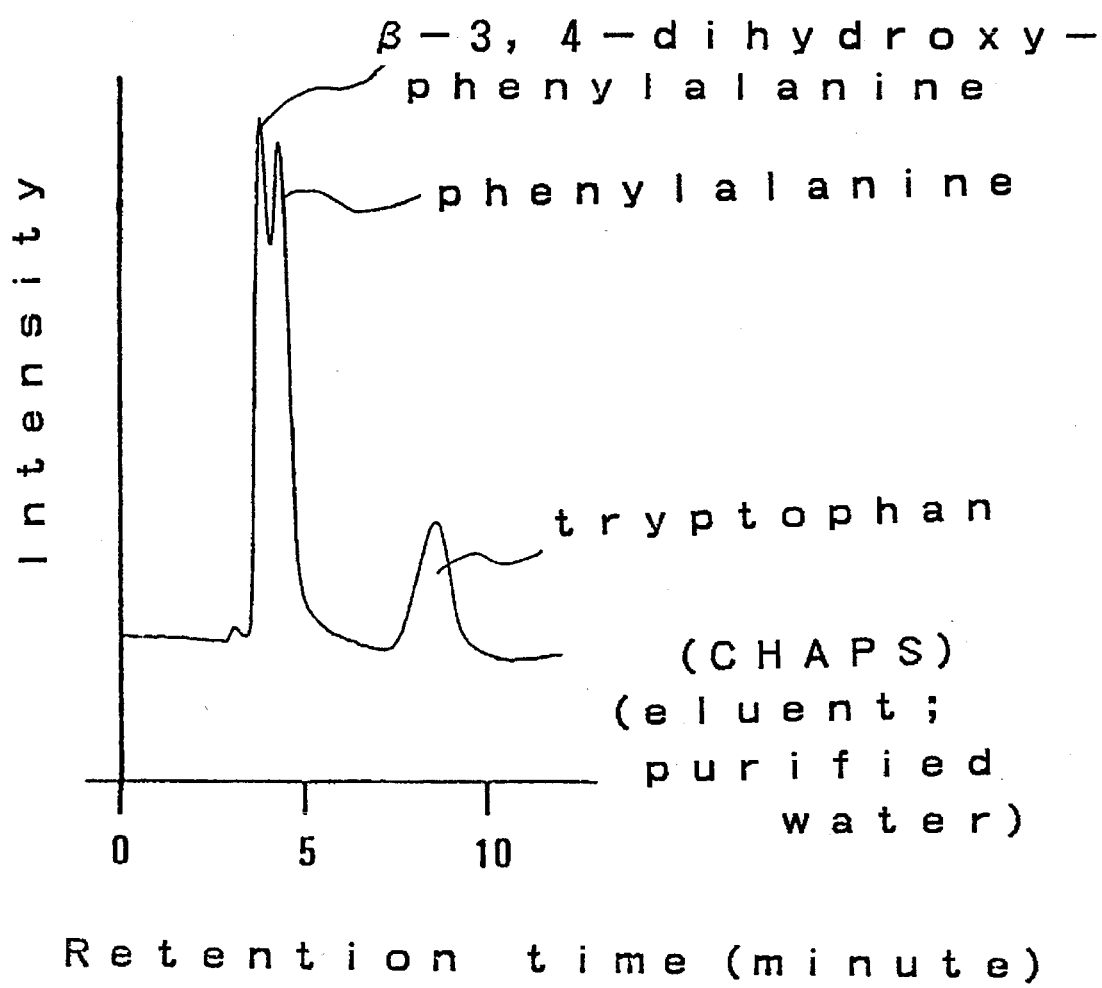
FIG. 12 is an explanatory view depicting the chromatogram from the analysis of three species of UV-absorptive amino acids, using CHAPS micellar coated stationary phase and purified water as an eluent in Example.

Under the conditions that the eluent was purified water and the zwitterionic surfactant to be used in the separation column was CHAPS, three species of UV-absorptive organic zwitterions (amino acids, ie. (1) β-3,4-dihydroxy phenylalanine, (2) phenylalanine and (3) tryptophan) were analyzed. FIG. 12 shows the chromatogram. The results indicate that the three species of individual amino acids were separated well using water as the eluent.

(5) Phosphate buffer solution as eluent

Figure 13:
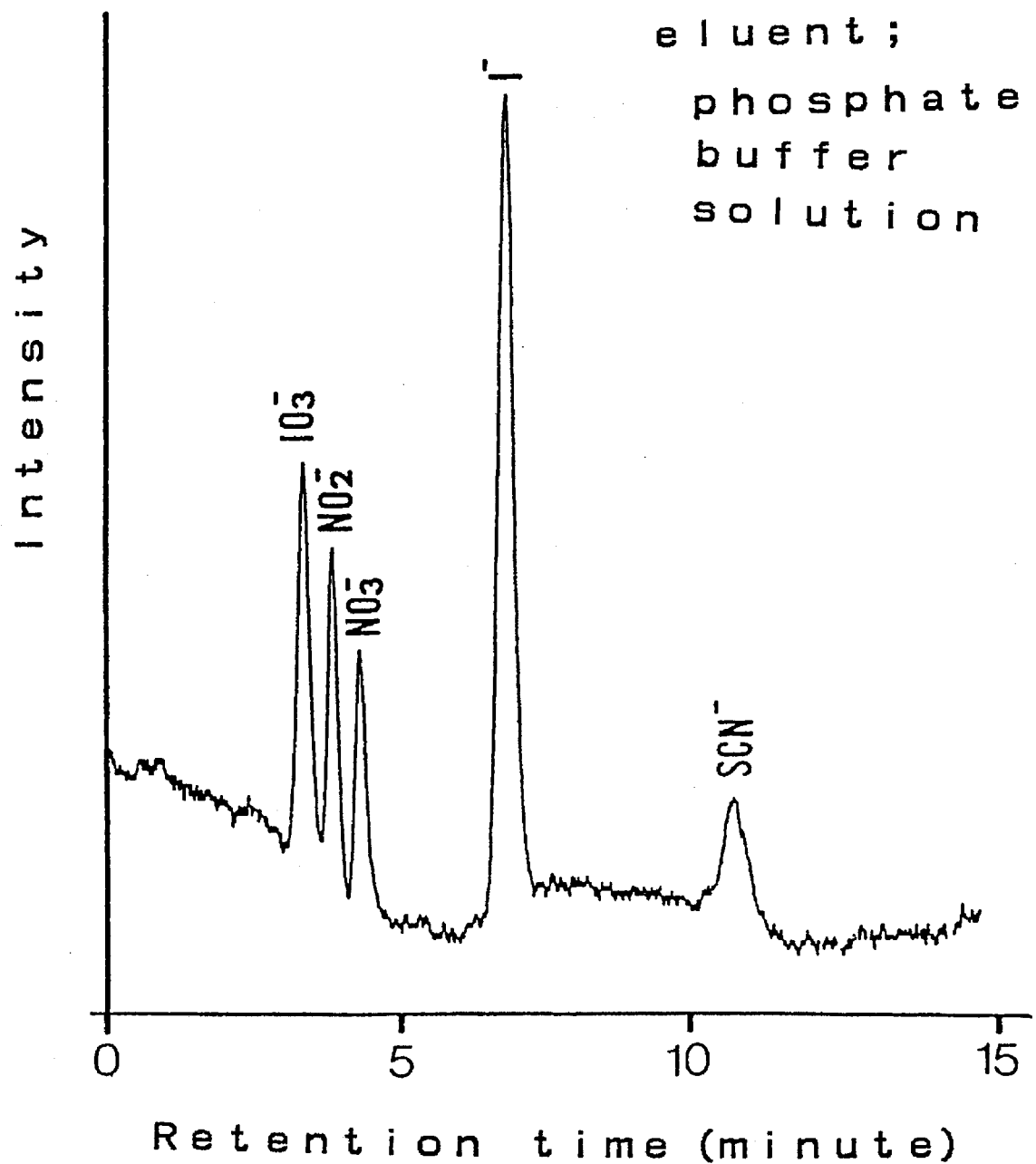
FIG. 13 is an explanatory view depicting the chromatogram from the analysis of five species of UV-absorptive inorganic anions, using CHAPS micellar coated stationary phase and phosphate buffer as an eluent in Example.

Except for the use of aqueous phosphate buffer solution ($NaH_2PO_4$ 10 mmol+$Na_2HPO_4$ 10 mmol/liter) in place of purified water and the use of five species of inorganic anions ($IO_3^-$, $NO_2^-$, $NO_3^-$, $I^-$ and $SCN^-$) as the analyte ions, analysis was done following the same fashion as in what is described above in aforementioned (2). As shown in the chromatogram of FIG. 13, the individual ions were separated well consequently as in the case of purified water (FIG. 5).

Figure 14:
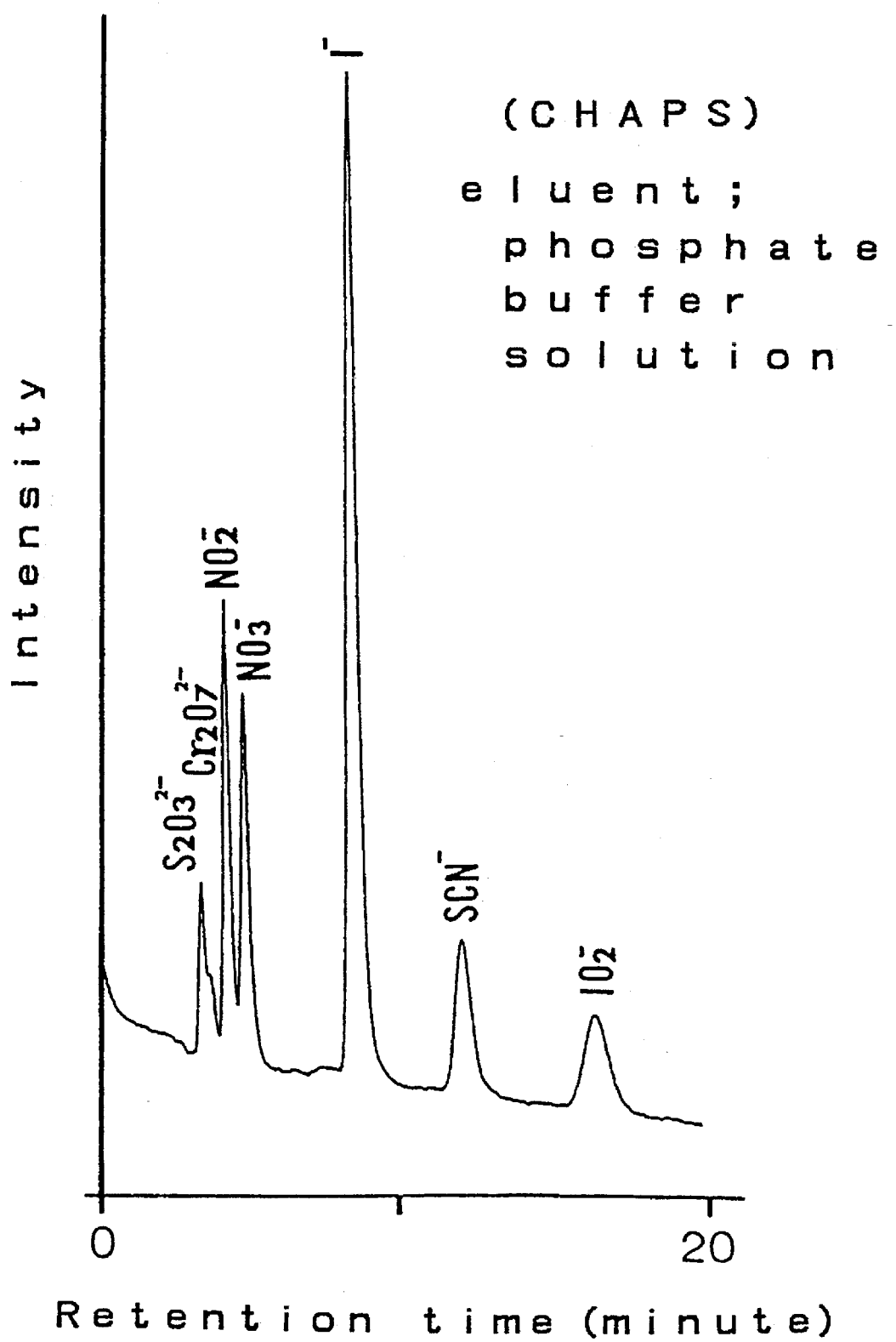
FIG. 14 is an explanatory view depicting the chromatogram from the analysis of two species of divalent anions and five species of monovalent anions, using CHAPS micellar coated stationary phase and phosphate buffer as an eluent in Example.

Similarly, two species of divalent anions ($S_2O_3^-$ and $Cr_2O_7^-$) and five species of monovalent anions ($NO_2^-$, $NO_3^-$, $I^-$, $SCN^-$ and $IO_2^-$) were simultaneously analyzed. FIG. 14 shows the chromatogram. The results indicate that the individual divalent anions were eluted firstly, and the individual monovalent-anions were then eluted, and that good separation was achieved not only among the group of the individual monovalent anions but also among the group of the individual divalent anions, and additionally that good separation was confirmed among the monovalent and divalent anions.

Figure 15:
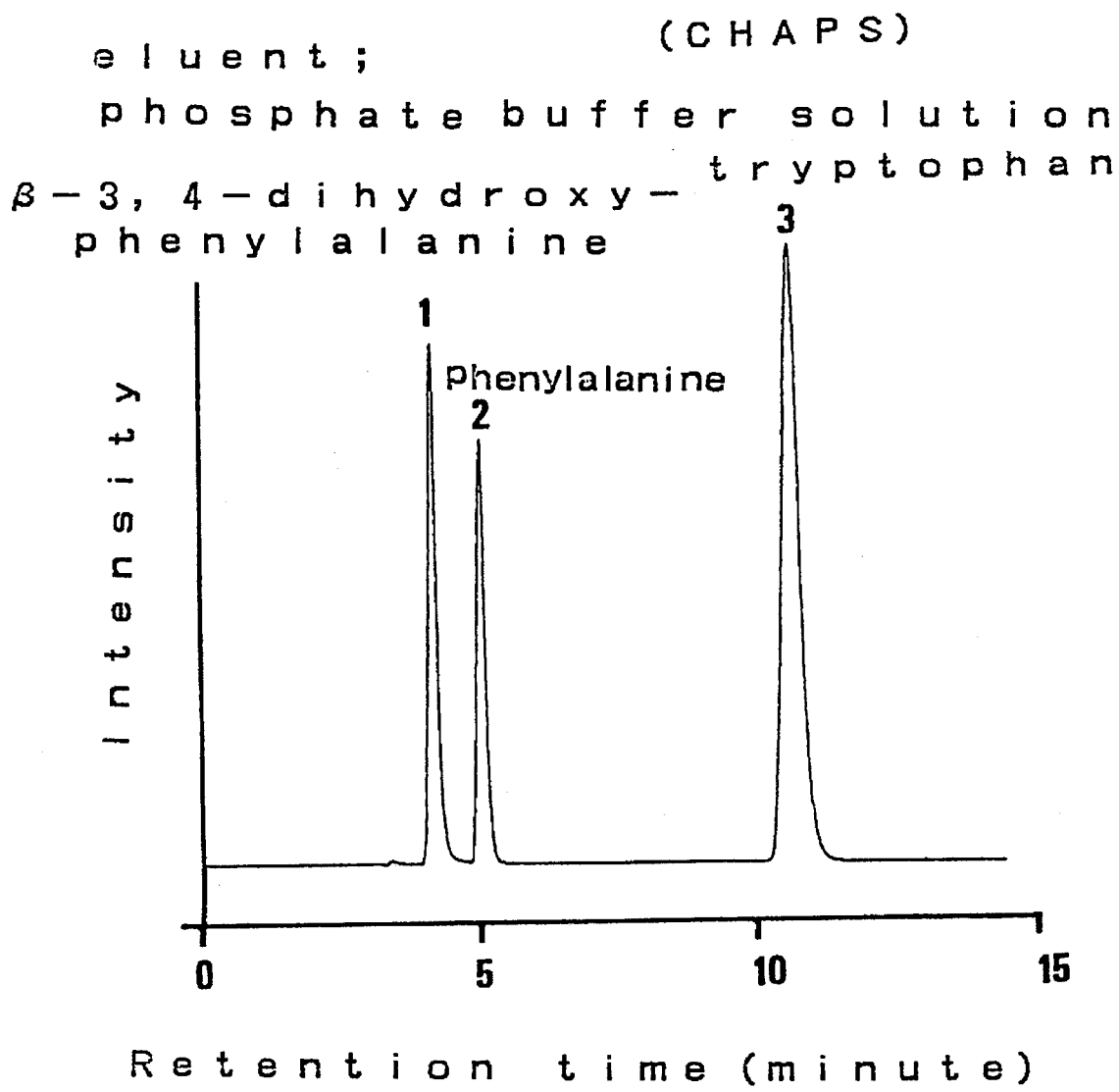
FIG. 15 is an explanatory view depicting the chromatogram from the analysis of three species of amino acids, using CHAPS micellar coated stationary phase and phosphate buffer in Example.

Furthermore, three species of amino acids used in the above (4) were analyzed, and FIG. 15 shows the chromatogram. The results indicate that the individual amino acids were separated well from each other as in the case of purified water (FIG. 12).

(6) Relationships between ion concentration in eluent and retention time

Figure 16:
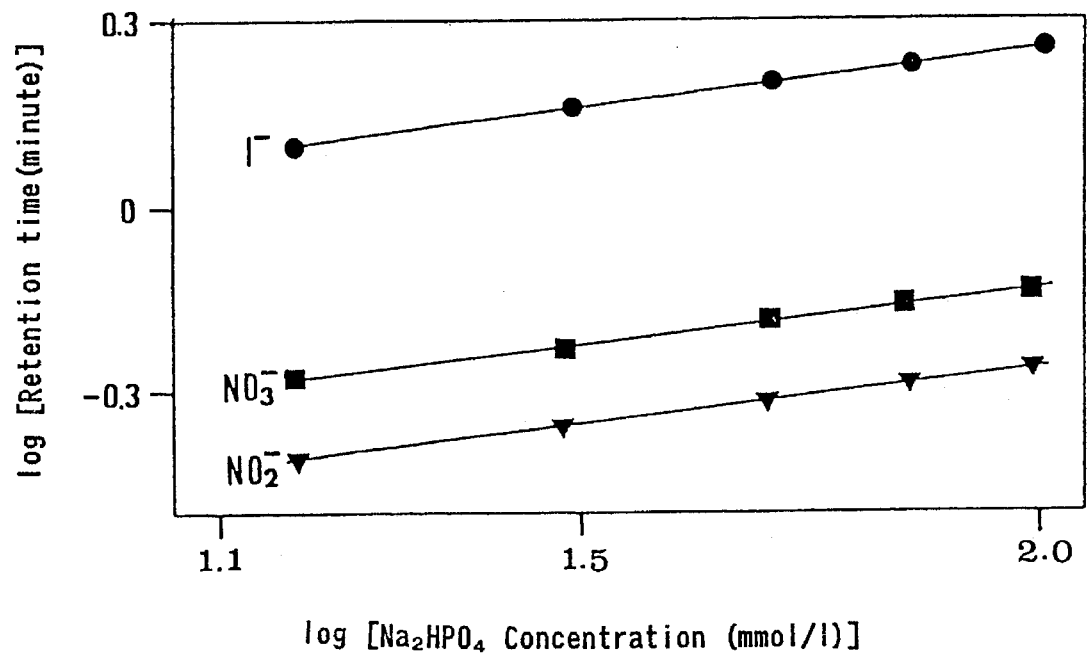
FIG. 16 is a graph depicting the relationships between the concentration of disodium hydrogenphosphate in an eluent, ie. an aqueous disodium hydrogenphosphate solution and the retention time in Example.

The same procedure was followed, except that (1) disodium hydrogenphosphate solution (FIG. 16), (2) copper (II) sulfate solution (FIG. 17) and (3) the phosphate buffer solution (FIG. 18) described above as the eluents were used, and that monovalent anions each ($NO_2^-$, $No_3^-$, $SCN^-$ and $IO_3^-$) were used and that the ion concentration of each of the eluents was modified. The results are shown in FIGS. 11, 12 and 13 respectively. All of the results indicate very interesting relationship. That is, the retention time is prolonged as the increase in the ion concentration in an eluent. By general ion chromatography, adversely, the retention time gets shorter as the increase in the ion concentration (J. Chromatogr., 122(1976) 17–34). In the present Example, however, the results are totally adverse to what is described above.

(7) Indirect measurement of UV-non-absorptive anions

UV detectors cannot detect UV-non-absorptive ions. Therefore, indirect UV absorption detection method (referred to as "indirect detection method" hereinafter) was examined for the analysis of multiple UV-non-absorptive ions or multiple ions containing UV-non-absorptive ions.

Figure 19:
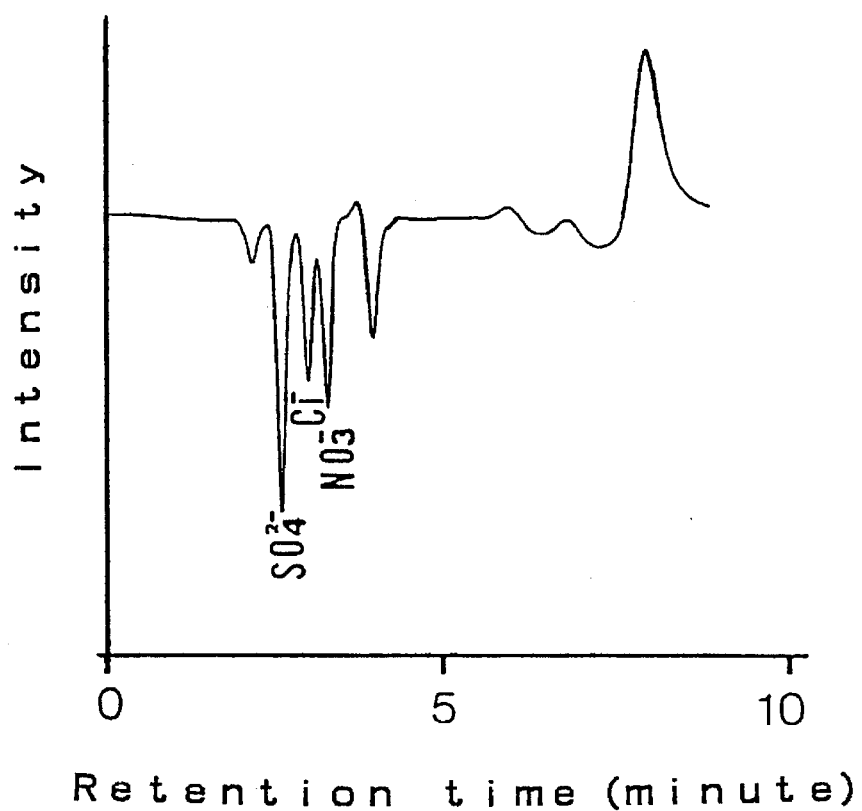
FIG. 19 is an explanatory view of the chromatogram where sulfate ion, chloride ion and nitrate ion are detected by indirect absorption detection method.

Firstly, $NO_3^-$, $Cl^-$ (UV-non-absorptive) and $SO_4^{2-}$ (UV-non-absorptive) were used as anions; as a photoabsorptive mobile phase, a sodium salicylate solution (1 mmol sodium salicylate dissolved in 1 liter of an aqueous 5 vol % acetonitrile solution) was used. The results of the analysis are shown in FIG. 19. As shown in the figure, the UV-non-absorptive anions were separated well, with excellent UV detection.

Using NaTC instead of NaTDC, nearly the same chromatogram was generated (not shown).

Figure 20:
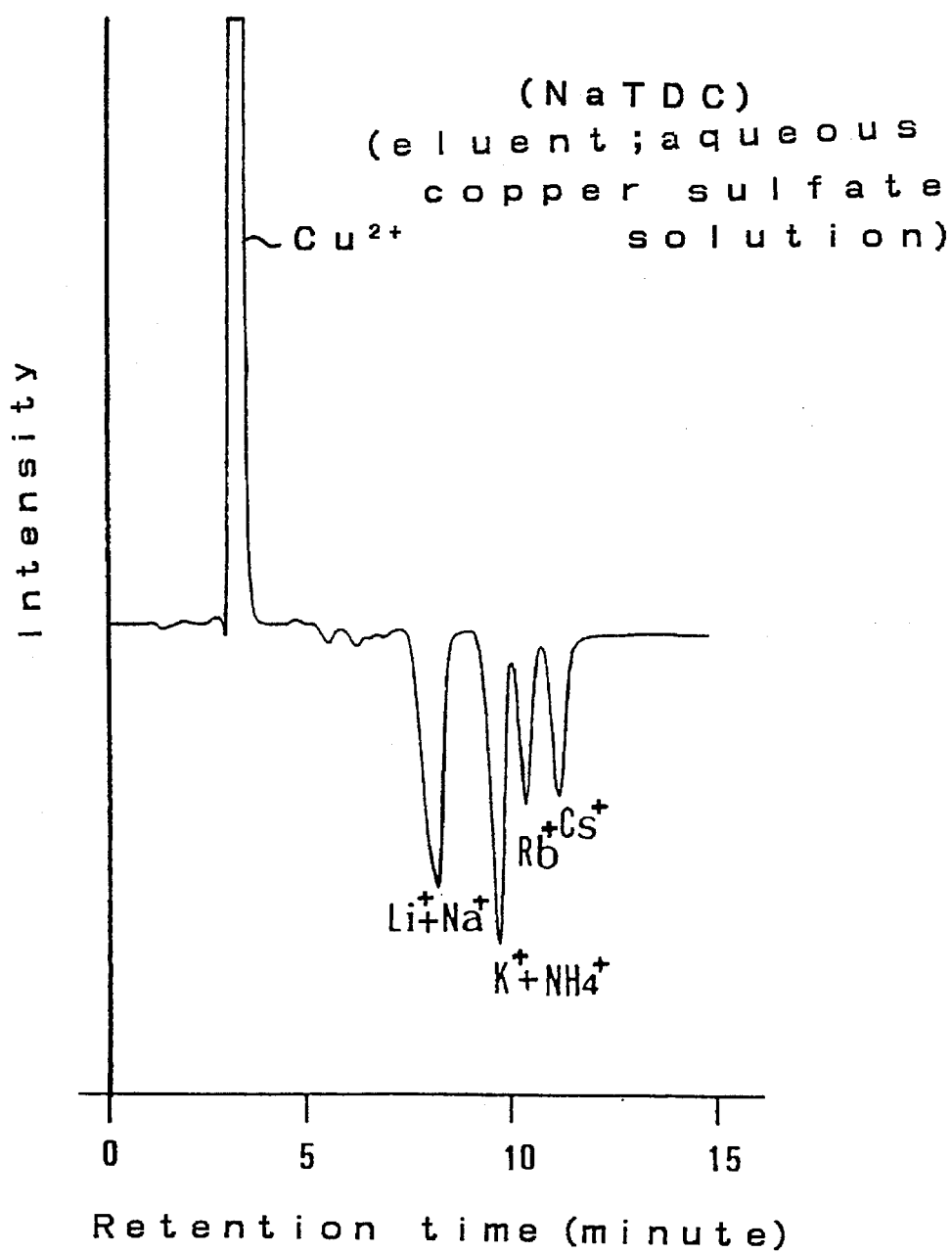
FIG. 20 is an explanatory view of the chromatogram where the cations separated by using NaTDC micellar stationary phase and an eluent, ie. aqueous copper sulfate solution, are detected by indirect detection method in Example.

Secondly $Li^+$, $Na^+$, $K^+$, $NH_4^+$, $Rh^+$ and $Cs^+$ (all UV-non-absorptive) were used as cations, and as a photoabsorptive mobile phase, copper sulfate (UV-absorptive $CU^{2+}$) was used. And NaTDC was used as zwitterionic surfactant. Following the same procedure, analysis was done. The results are shown in FIG. 20. As in the case of the anions described above, the individual UV-non-absorptive cations were separated well (however, $Li^+$ was not separated from $Na^+$; $K^+$ was not separated from $NH_4^+$). The UV detector worked well for the detection.

(8) Types of zwitterionic surfactants

In order to test the electrostatic effect of the zwitterionic stationary phase formed on the surface, two types of zwitterionic stationary phases were used. One was an ODS solid phase onto which CHAPS micellar particles were coated and formed (referred to as "CHAPS stationary phase"), while the other was an ODS solid phase onto which NaTDC micellar particles were coated and formed (referred to as "NaTDC stationary phase"). The former is provided with a sulfonate anion portion and an ammonio cation portion. The nitrogen atom of the amide group of the latter shows more or less positive charge (partially positive charge:$\delta^+$), which degree ($\delta^+$) is far lower than the negative degree of the anion (−), so that the negative charge has a larger effect in total.

Figure 17:
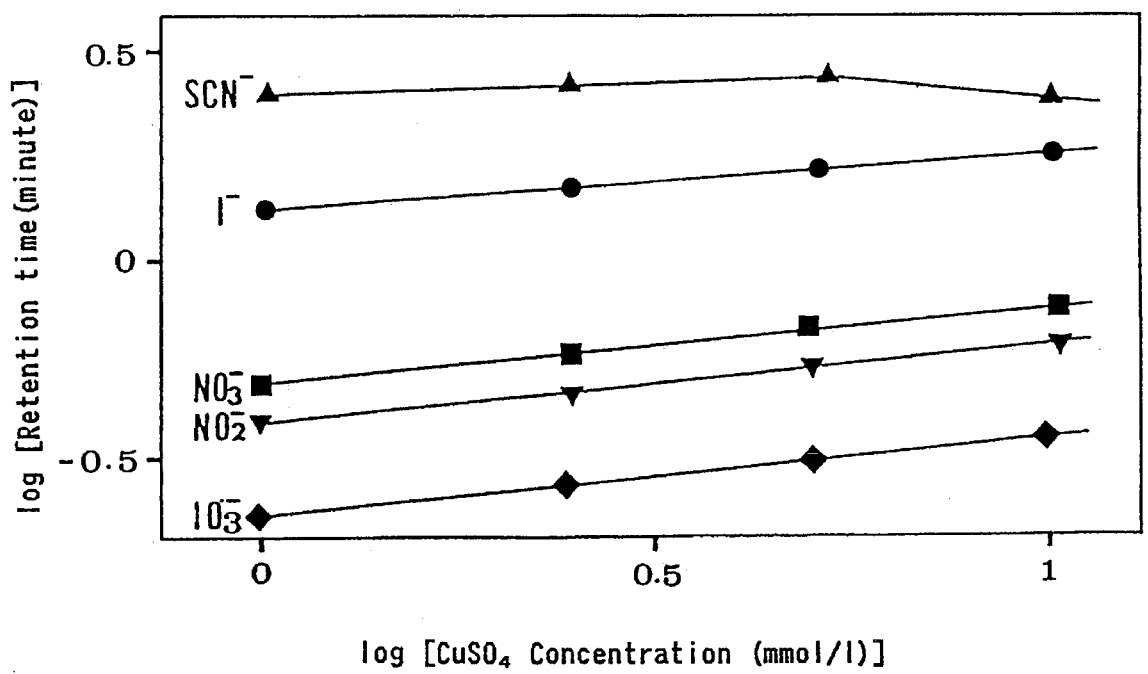
FIG. 17 is a graph depicting the relationships between the concentration of copper (II) sulfate in an eluent, ie. an aqueous copper (II) sulfate solution and the retention time in Example.
Figure 18:
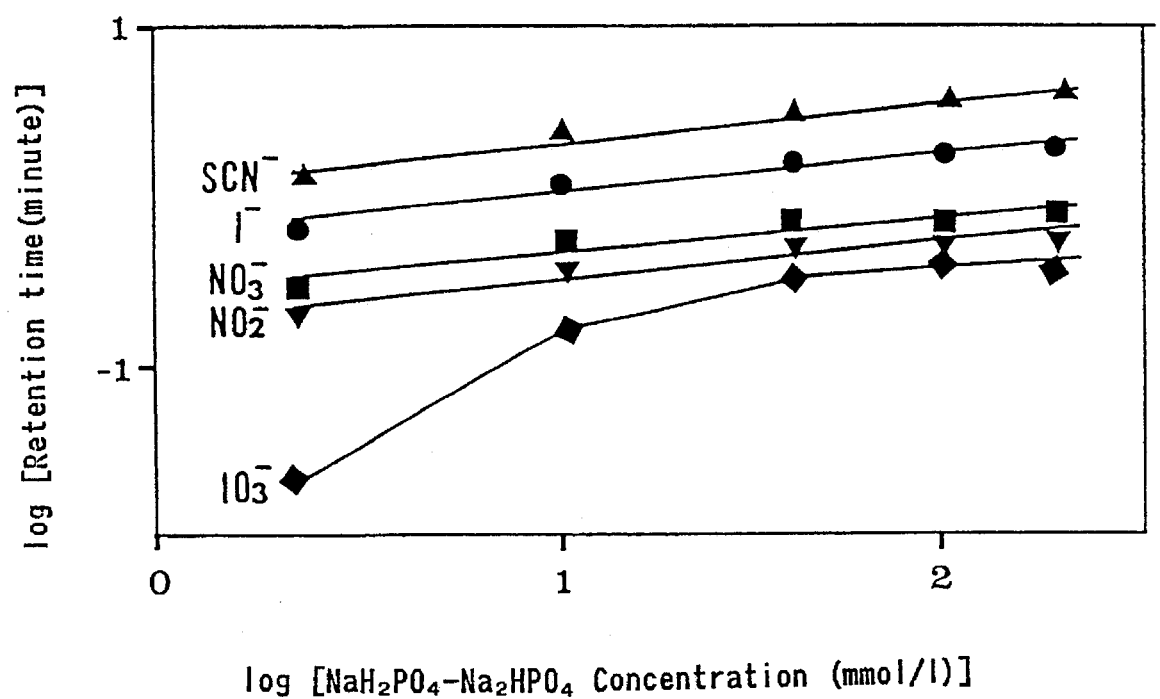
FIG. 18 is a graph depicting the relationships between the concentration of phosphate salts in an eluent, ie. an aqueous phosphate buffer and the retention time in Example.

Using firstly NaTDC stationary phase ($\delta^+$ . −), purified water as eluent, I− and $SCN^-$ as analyte ions and following the same procedure, analysis was effected. The results are shown in FIG. 17. These anions were directly detected via UV absorption. When the NaTDC stationary phase of a relatively higher negative charge was used, the retention time distinctively decreased as short as 4 minutes or less via the repulsion force, compared with the retention time of the chromatogram (FIG. 5) with CHAPS stationary phase, namely 12 minutes or less.

Figure 21:
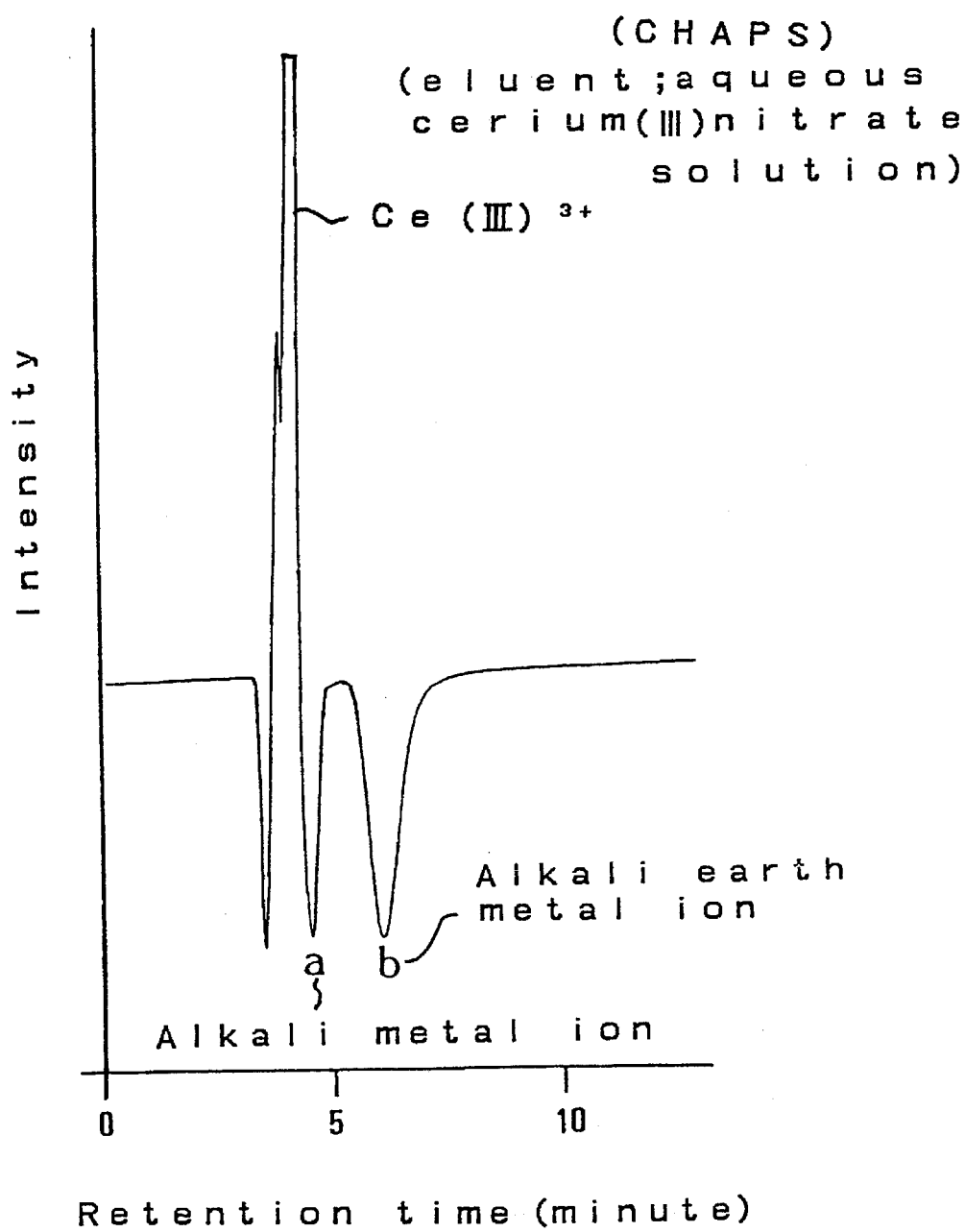
FIG. 21 is an explanatory view of the chromatogram where the cations separated by using CHAPS micellar stationary phase and an eluent, ie. aqueous cerium chloride solution, are detected by indirect detection method in Example.

Using secondly NaTDC stationary phase, $CuSO_4$ solution as eluent, $Li^+$, $Na^+$, $K^+$, $NH_4^+$, $Rb^+$ and $Cs^+$ as analyte ions and following the same procedure, analysis was effected. The result shown in FIG. 20. Using alternatively CHAPS stationary phase, $CuSO_4$ as eluent, $Li^+$, $Na^+$, $K^+$, $NH_4^+$, and $Cs^+$ as analyte ions and following the same procedure, analysis was effected. The result is shown in FIG. 21. These cations were detected by indirect detection method (in the analysis of FIG. 20, the UV absorption mobile phase was an aqueous copper sulfate solution; in the analysis of FIG. 21, the UV absorption mobile phase was an aqueous cerium (III) chloride solution).

In the NaTDC stationary phase, the monovalent cations each were separated substantially well within 8 to 12 minutes. In the CHAPS stationary phase with a possibly higher repulsion force from the cat ions via the higher positive charge, on the contrary, the separation among the monovalent cation group could not progress. The retention time was extremely short (about 4 minutes), indicating a poorer separation effect. Furthermore, the divalent cations each were eluted at about 6 minutes, and the separation among the divalent cation group was not observed.

The individual stationary phases are thus in the electrostatic states as has been described above, so the repulsion force from the anions in the NaTDC stationary phase ($\delta^+$ . –) gets larger relatively, leading to the acceleration of anion elution and adversely leading to the slowing down of cation elution. On the contrary, the CHAPS stationary phase shows an effect adverse to that of NaTDC stationary phase, namely, the acceleration of cation elution but the slowing down of anion elution. Hence, it can be said that the NaTDC stationary phase ($\delta^+$ . –) is suitable for cation separation, while the CHAPS stationary phase (+ . $\delta^+$ . –) is suitable for anion separation and cation separation. In any case, however, the retention time (separation potency) is under the control of the intensities of electrostatic attraction and repulsion forces from the combination of analyte ion species and a zwitterionic layer. Preferable retention time is therefore determined, depending on the negative and positive degrees at both of a positive-charge portion and a negative-charge portion of a stationary phase, the type of the analyte ion to be used, the type of an eluent and the like.

(9) Relationships between simultaneous separation of cations and anions and ion concentration in eluent or type of zwitterionic surfactant.

1. Ion Concentration in Eluent

Figure 22:
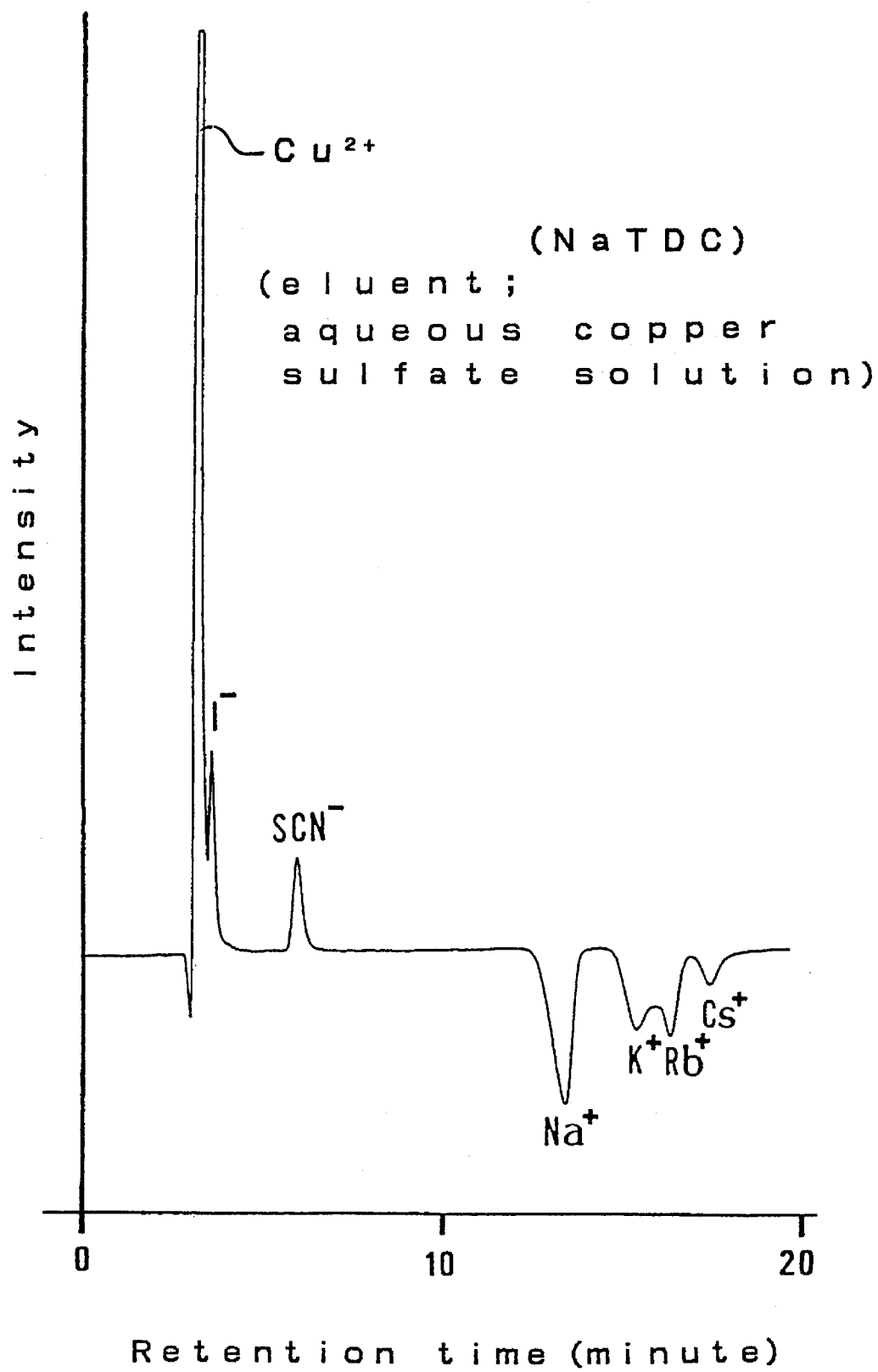
FIG. 22 is an explanatory view of the chromatogram where the anions and cations, simultaneously separated in Example by using NaTDC micellar stationary phase and an eluent, ie. aqueous copper sulfate solution, are detected by indirect detection method in Example.
Figure 23:
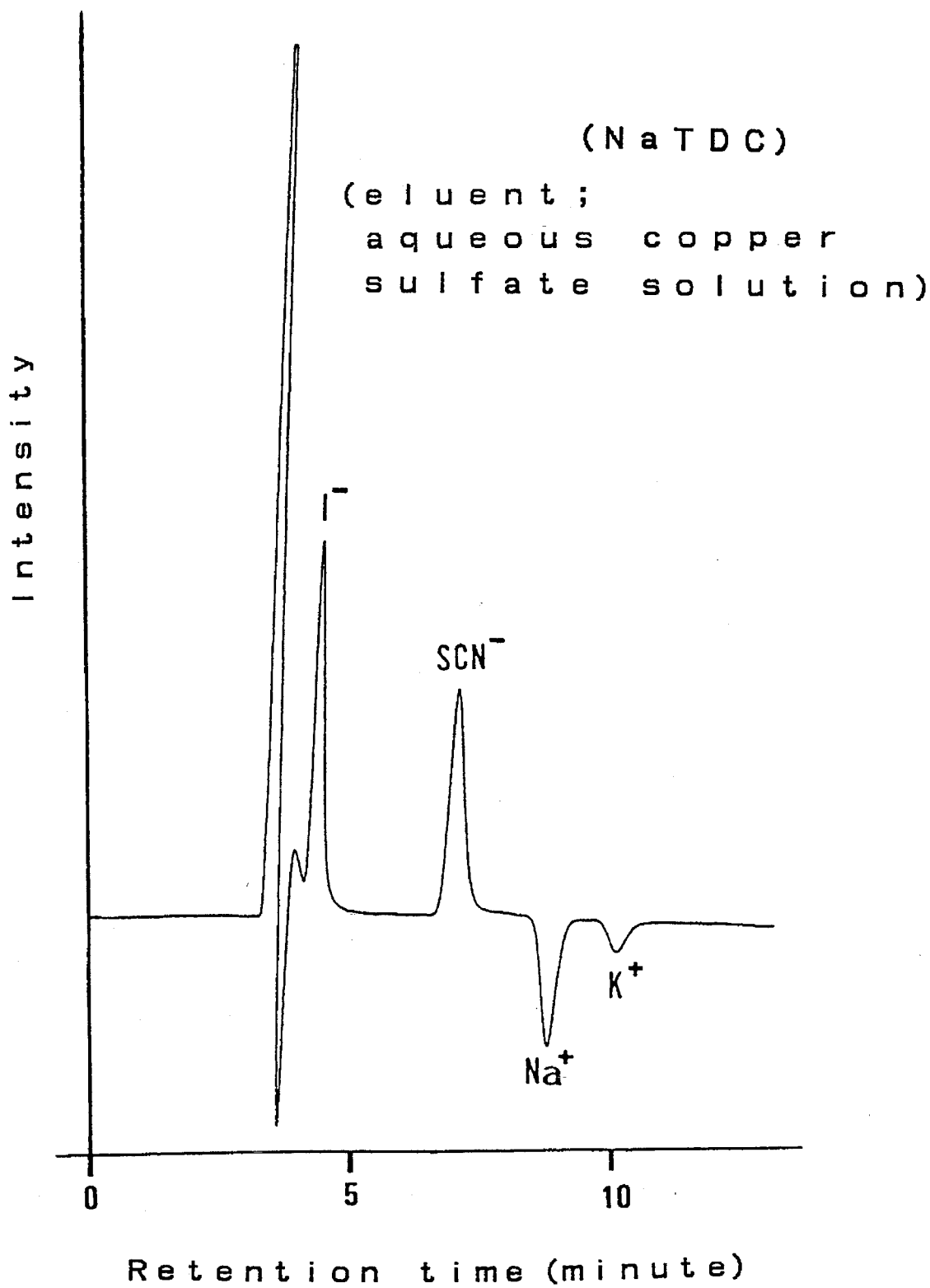
FIG. 23 is an explanatory view of the chromatogram where the anions and cations, simultaneously separated in Example by using NaTDC micellar stationary phase and an eluent, ie. aqueous copper sulfate solution of a higher ionic concentration, are detected by indirect detection method.

Analysis was done using NaTDC stationary phase, an aqueous copper sulfate solution of a concentration of 1 mmol/liter as a UV absorption mobile phase, and analyte ions of $I^-$, $SCN^-$, $Na^+$, $K^+$, $Rb^+$ and $Cs^+$. The chromatogram is shown in FIG. 22. Using the same stationary phase and the same UV absorption mobile phase of a concentration of 5 mmol/liter and using analyte ions of $I^-$, $SCN^-$, $Na^+$ and $K^+$, analysis was effected. The chromatogram is shown in FIG. 23. In both of the analyses, the anions were detected via the UV absorption of themselves, while the cations were detected by the indirect detection method.

These results indicate that each of the cations and the anions were separated well in any case, suggesting excellent separation performance. As the increase in the ion concentration in the eluents, furthermore, the anions in common to the above two analyses got longer retention times ($I^-$, about 4 minutes>about 3 minutes; $SCN^-$, about 7 minutes>about 6 minutes), while the cations in common got shorter retention times ($Na^+$, about 9 minutes<about 13 minutes; $K^+$, about 10 minutes<about 15 minutes).

2. Types of Zwitterionic Surfactants

Figure 24:
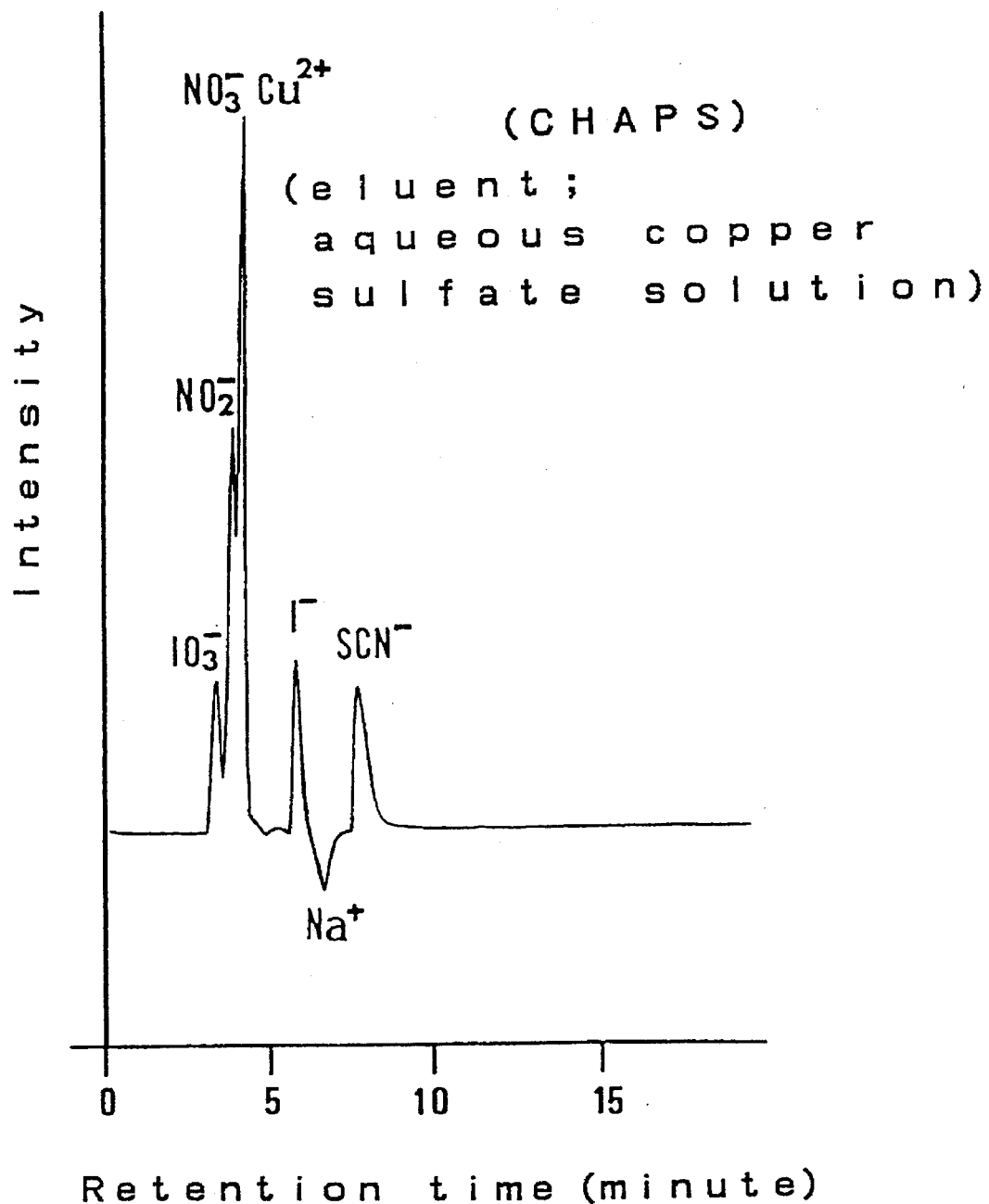
FIG. 24 is an explanatory view of the chromatogram where the anions and cations, simultaneously separated in Example by using CHAPS micellar stationary phase and an eluent, ie. aqueous copper sulfate solution, are detected by indirect detection method.

Analysis was done using CHAPS stationary phase, an aqueous copper sulfate solution of the same concentration as shown in FIG. 22 as a UV absorption mobile phase, and analyte ions of $I^-$, $SCN^-$, $NO_2^-$, $NO_3^-$, $IO_3^-$ and $Na^+$. The chromatogram is shown in FIG. 24. The results indicate that, although the anions and cations each were separated well, the retention time of each got closer compared with the case shown in FIG. 22, suggesting poorer separation performance.

3. Summary of Results

All of the ions were separated well in any case, which indicates that a variety of objective analyte ions can be analyzed well if an appropriate electrostaticity is selected. In CHAPS stationary phase, (+ . $\delta^+$ . – structure, FIG. 20), the elution of anions is slower ($I^-$, about 6 minutes>about 3 minutes; $SCN^-$, about 8 minutes>about 6 minutes) involving faster elution of cations ($Na^+$, about 6 minutes<about 13 minutes), via the difference from the $\delta^+$ . – structure of the NaTDC stationary phase (FIG. 22). Therefore, in CHAPS stationary phase, as shown in FIG. 24, the retention times of anions and cations get closer to each other.

As shown in the two examples, furthermore, cations and anions are simultaneously detected on one chromatogram, which is extremely novel with interesting results.

(10) Separation of α-amylase

Figure 25:
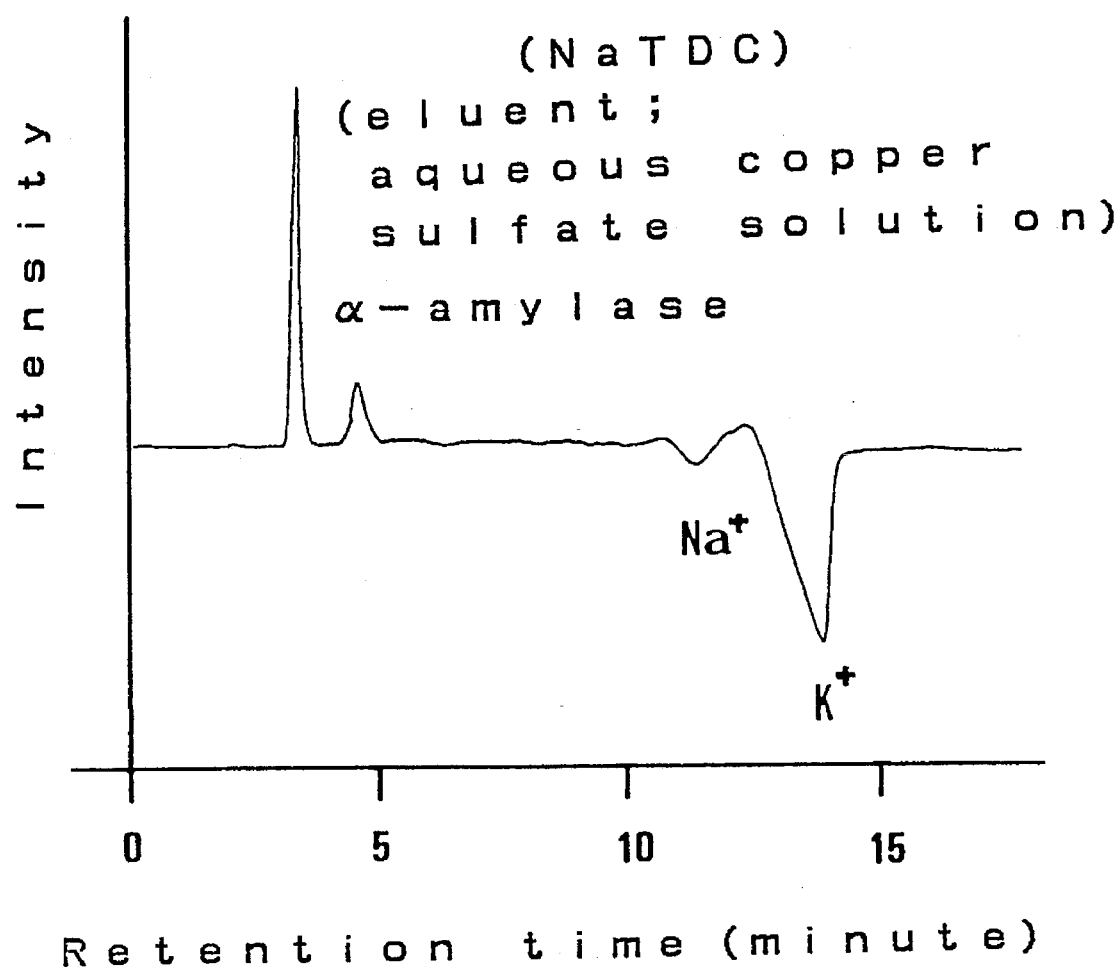
FIG. 25 is an explanatory view depicting the chromatogram from the analysis of α-amylase and two species of inorganic cations, using NaTDC micellar stationary phase and aqueous copper sulfate solution as an eluent in Example.

Under the conditions that the eluent was aqueous copper sulfate solution and the zwitterionic surfactant was NaTDC, α-amylase and two species of inorganic ions ($Na^+$ and $K^+$) were analyzed. FIG. 25 shows the chromatogram. The results indicate that the elution of α-amylase of large molecule is faster than the elution of cations. Therefore this stationary phase acts as a stationary phase having size exclusion property.

Figure 26:
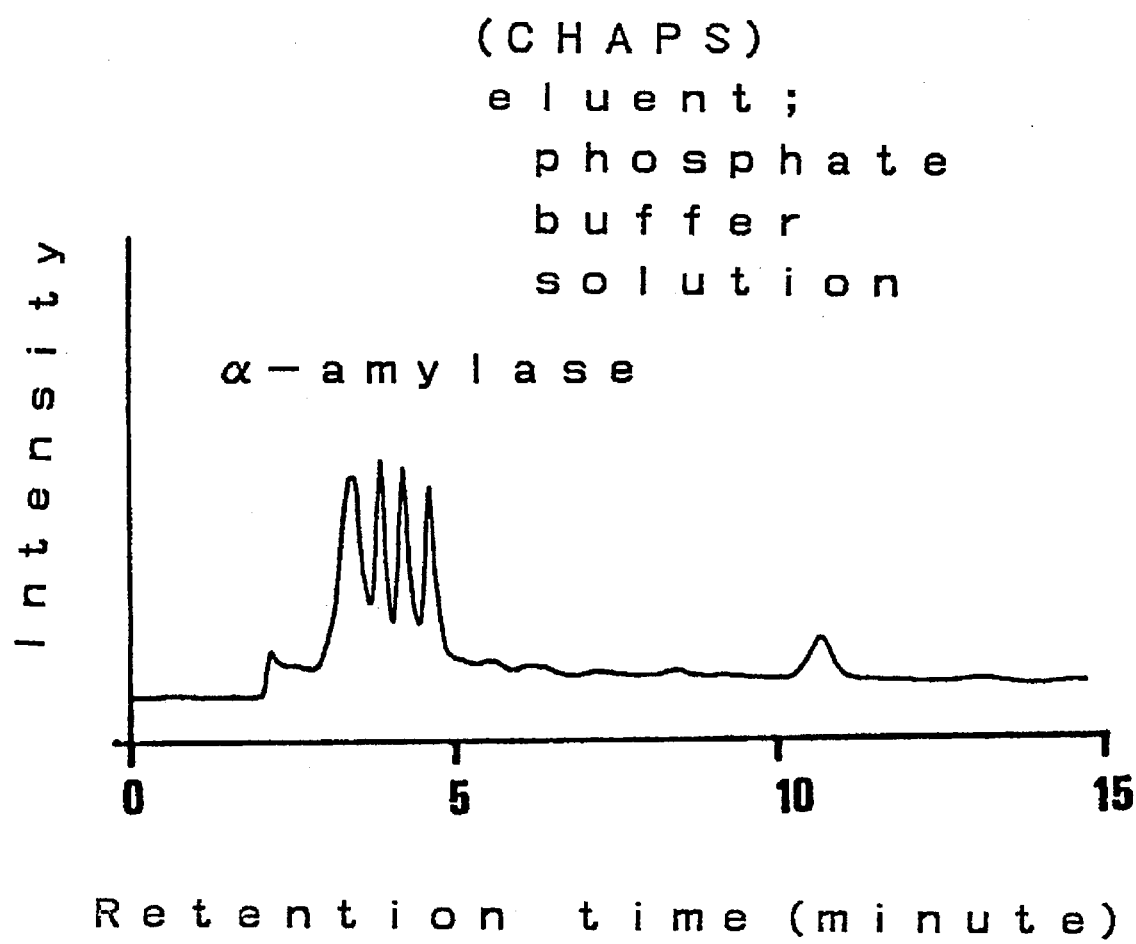
FIG. 26 is an explanatory view depicting the chromatogram from the analysis of α-amylase, using CHAPS micellar stationary phase and phosphate buffer as an eluent in Example.

Furthermore under the conditions that the eluent was phosphate buffer and the zwitterionic surfactant was CHAPS, α-amylase were analyzed. FIG. 26 shows the chromatogram. The results indicate that α-amylase has four main peaks within 3 to 5 minutes, and all components of α-amylase were eluted within 12 minutes. These results indicate that α-amylase was eluted rapidly.

(11) Use of two kind of bile surfactant

Figure 27:
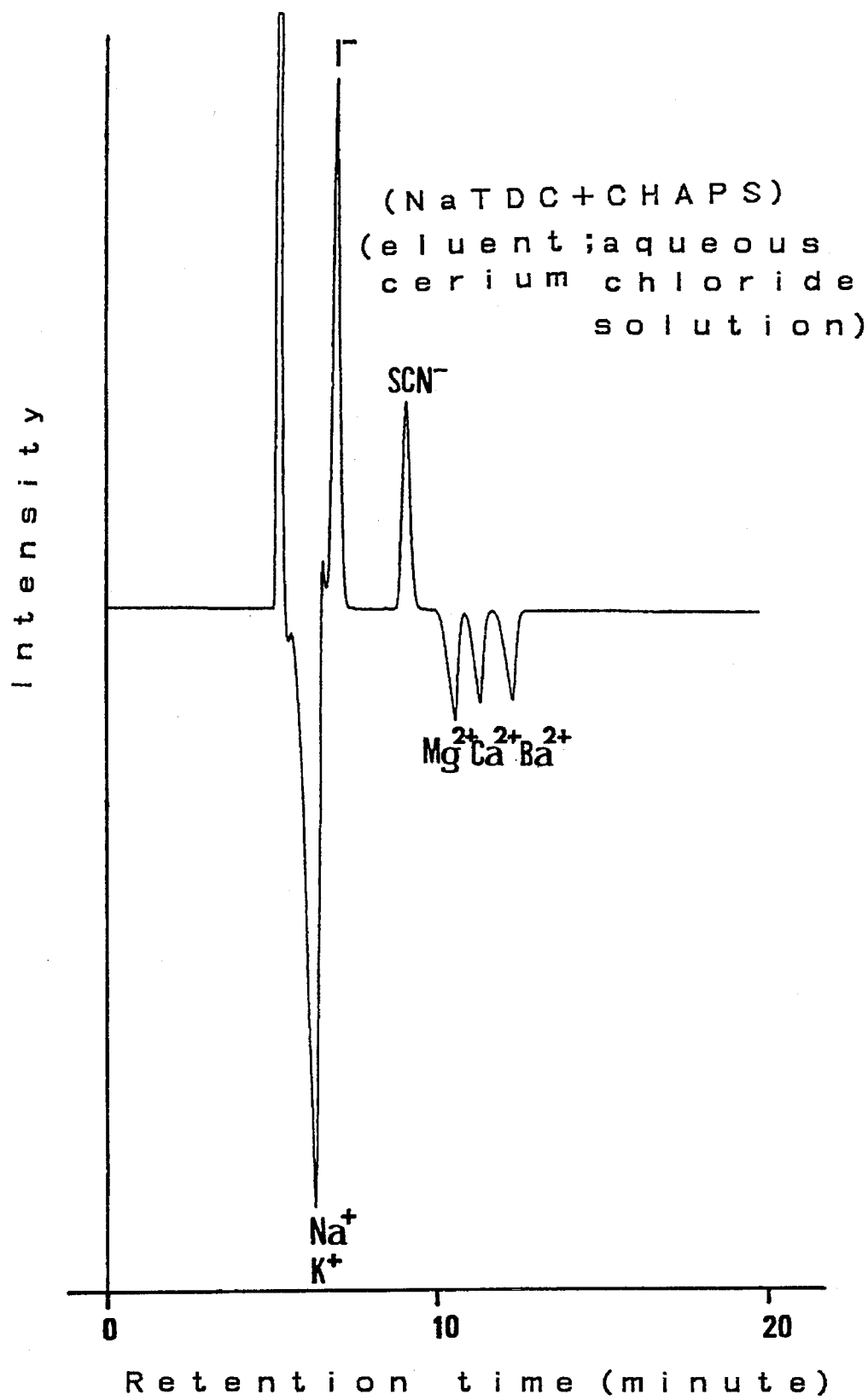
FIG. 27 is an explanatory view depicting the chromatogram from the analysis of five species of inorganic cations and two species of inorganic anions, using NaTDC-CHAPS mixed micellar stationary phase and aqueous cerium chloride solution as an eluent in Example.

Under the conditions that the zwitterionic stationary phase is formed using mixed bile micelles (NaTDC and CHAPS), five species of inorganic cations and three species of anions were analyze simultaneously. FIG. 27 shows the chromatogram. In this case the eluent was 2 mM of aqueous cerium chloride solution and detection wave length was 253 nM. The results indicate that another ions were separated well except separation between group of $Na^+$ and $K^+$.

Figure 28:
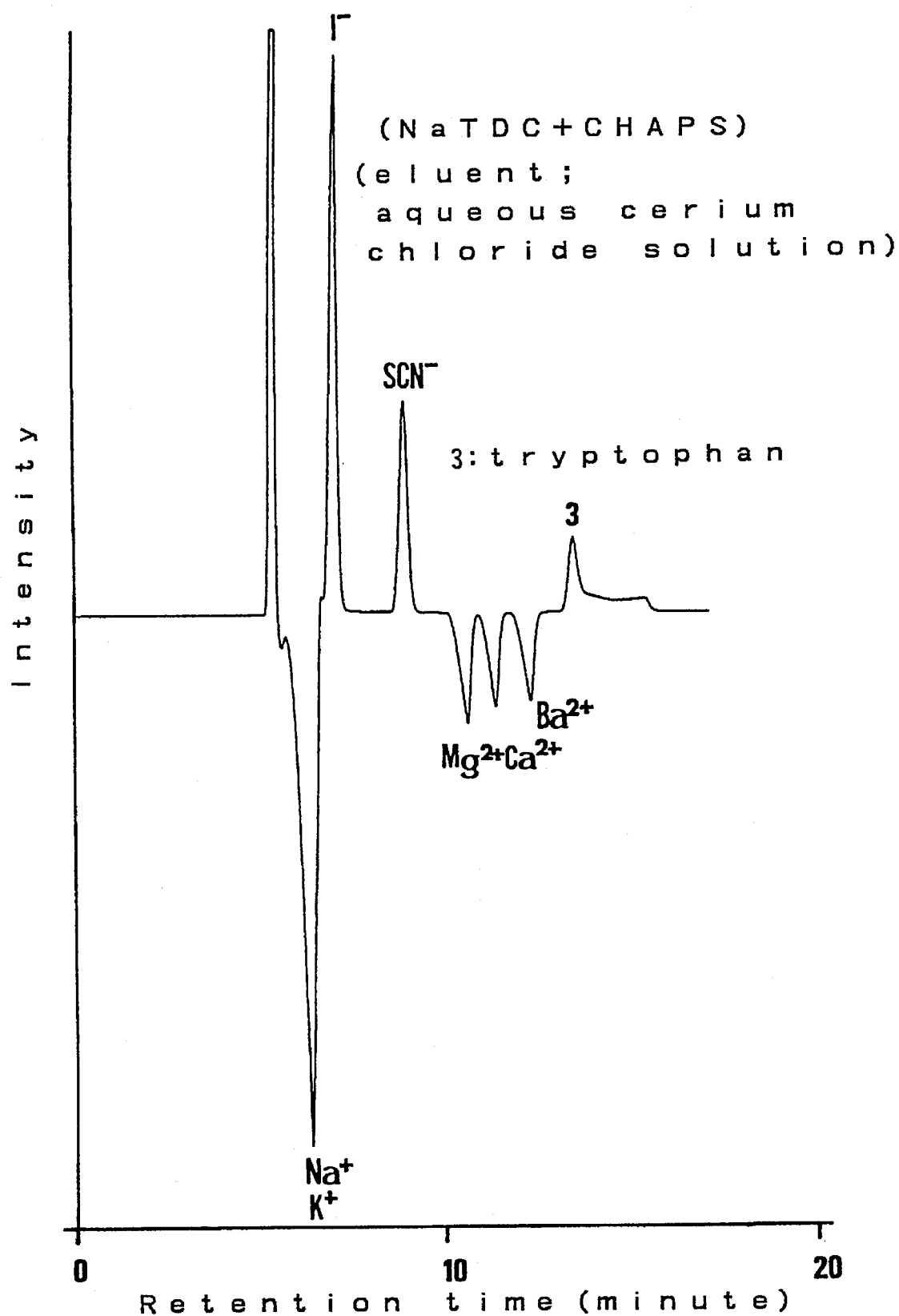
FIG. 28 is an explanatory view depicting the chromatogram from the analysis of anions, cations and tryptophan, using NaTDC-CHAPS mixed micellar stationary phase and aqueous cerium chloride solution as an eluent in Example.
Figure 29:
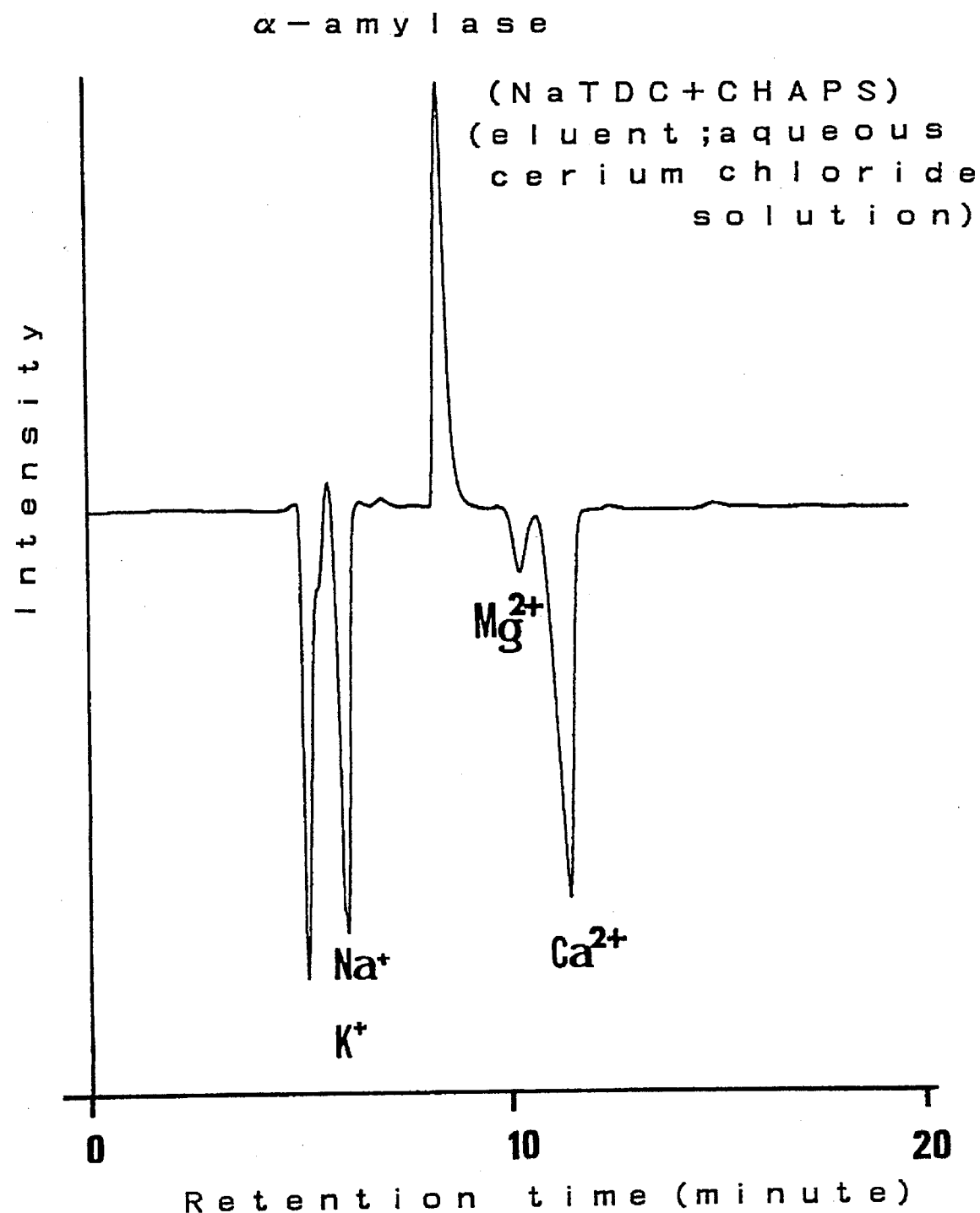
FIG. 29 is an explanatory view depicting the chromatogram from the analysis of cations and α-amylase, using NaTDC-CHAPS mixed micellar stationary phase and aqueous cerium chloride solution as an eluent in Example.

And abovementioned ions and tryptophan were analyze in the same way. FIG. 28 shows the chromatogram. The results indicate that tryptophan was separated well from another ions. Futhurmore α-amylase and four species of inorganic cations were analyze in the same way. FIG. 29 shows the chromatogram. The results indicate that α-amylase were separated well from another ions. And FIG. 28 and FIG. 29 shows that indivial retention time of α-amylase (protein), tryptophan (amino acid) and another inorganic ions was different one another, therefore the indivial compounds were separated well.

(12) Analysis of human saliva, urine and serum

① Analysis of Human Saliva

Figure 30:
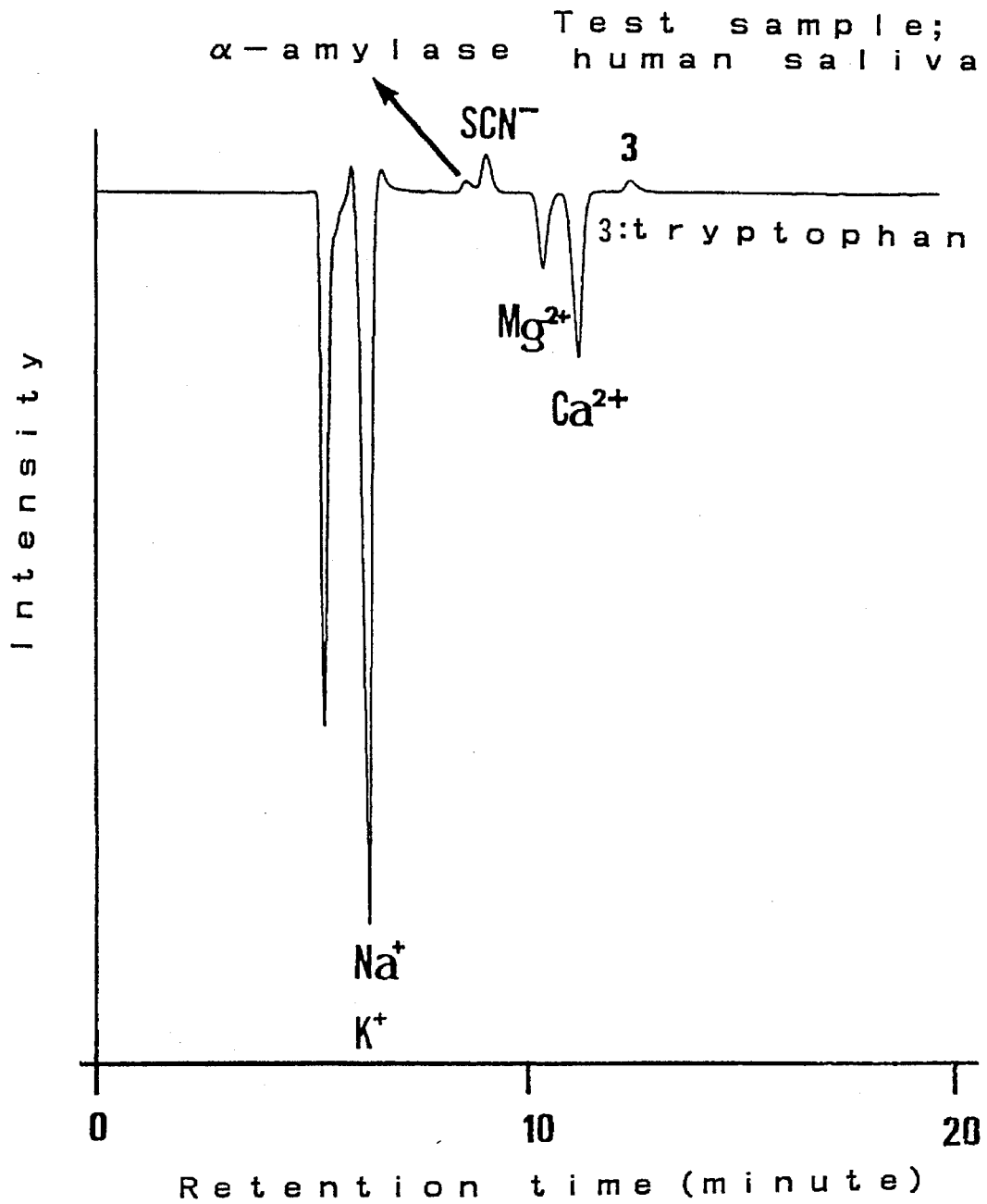
FIG. 30 is an explanatory view depicting the chromatogram from the analysis of human saliva, using NaTDC-CHAPS mixed micellar stationary phase and aqueous cerium chloride solution as an eluent in Example.
Figure 31:
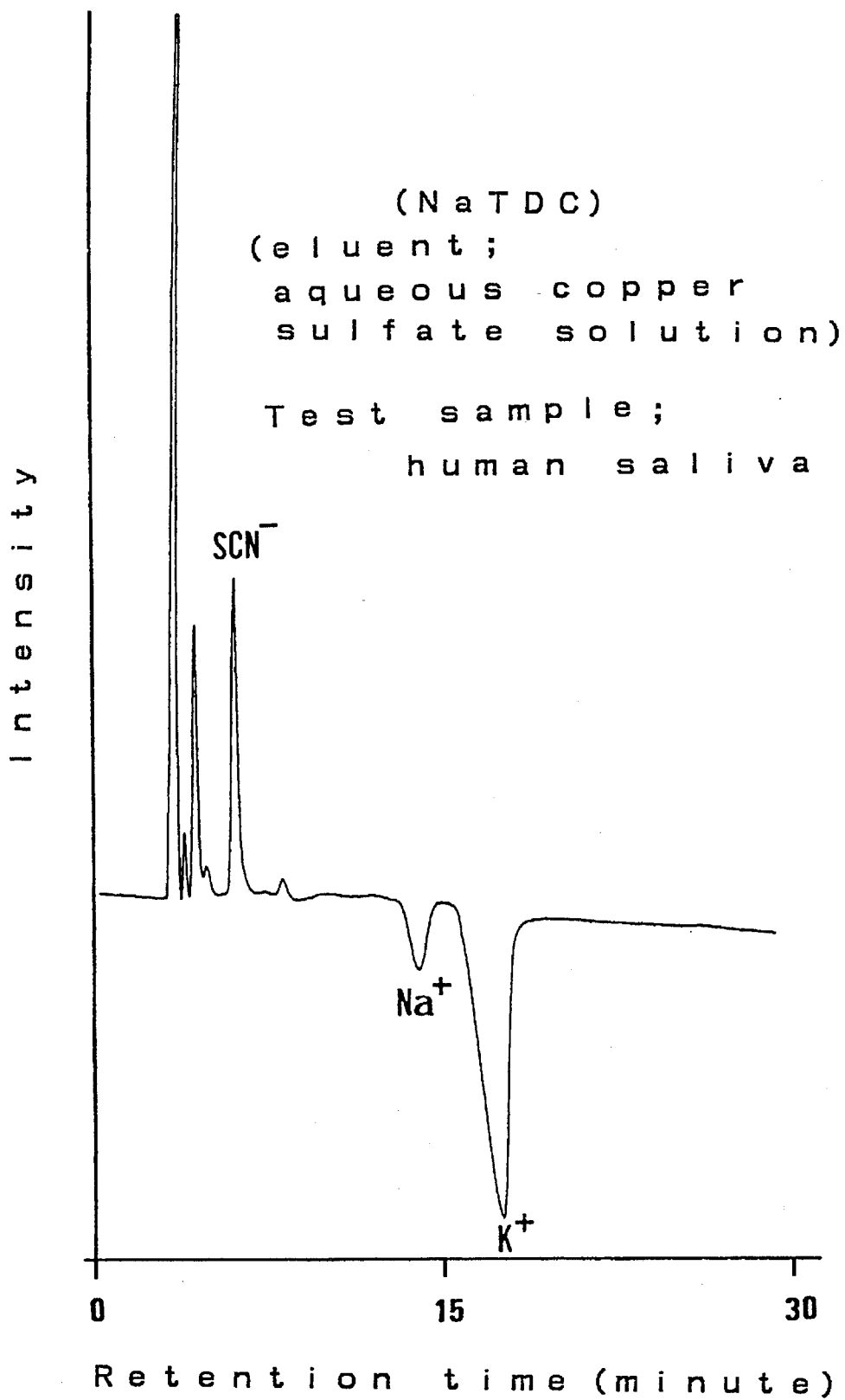
FIG. 31 is an explanatory view depicting the chromatogram from the analysis of human saliva, using NaTDC micellar stationary phase and aqueous copper sulfate solution as an eluent in Example.
Figure 32:
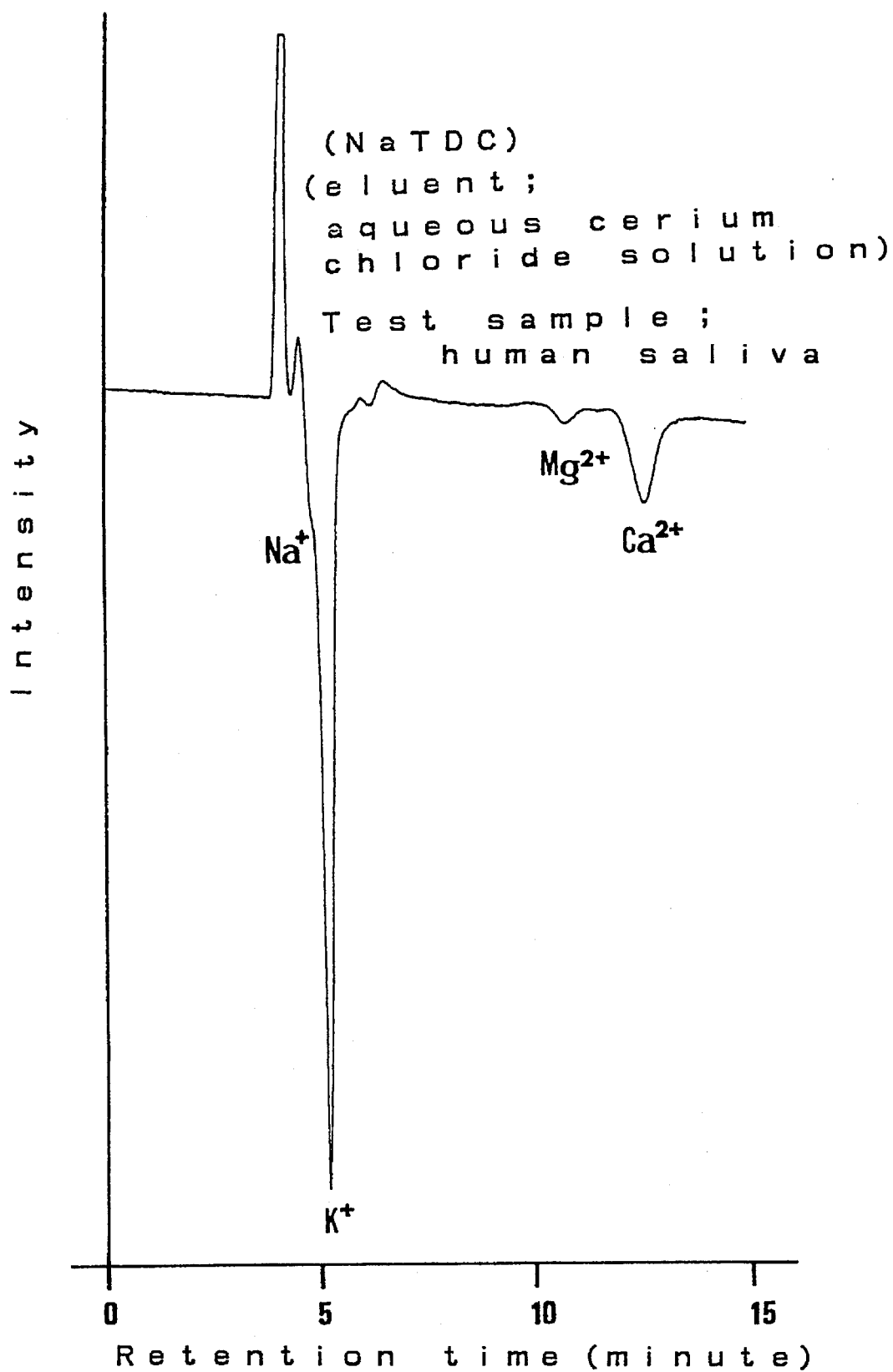
FIG. 32 is an explanatory view depicting the chromatogram from the analysis of human saliva, using NaTDC micellar stationary phase and aqueous cerium chloride solution as an eluent in Example.
Figure 33:
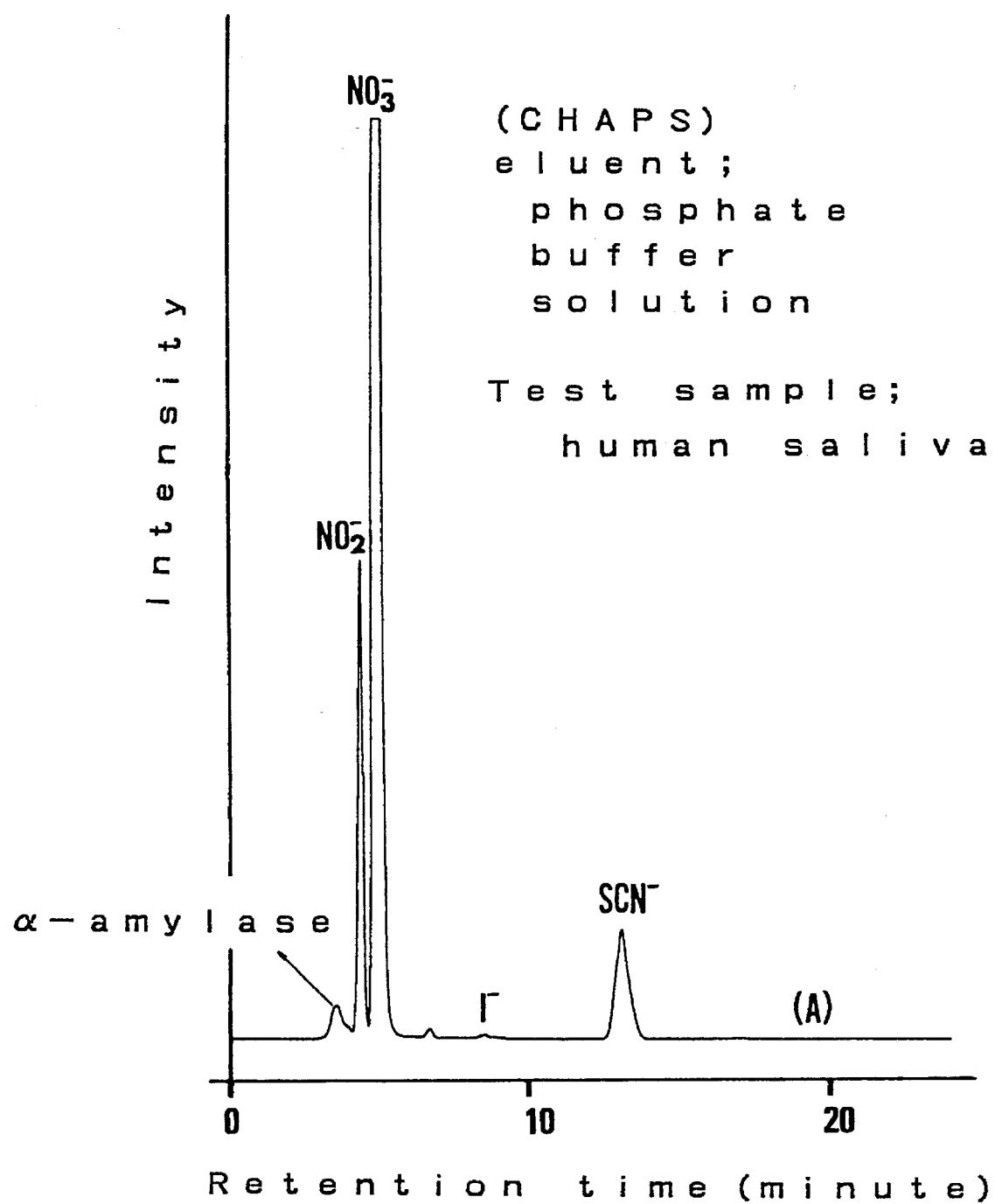
FIG. 33 is an explanatory view depicting the chromatogram from the analysis of human saliva, using CHAPS micellar stationary phase and phosphate buffer as an eluent in Example.

Under the conditions of aqueous cerium chloride solution as the eluent and NaTDC-CHAPS solid phase, human saliva was analyzed. The chromatogram is shown in FIG. 30. Under the conditions of aqueous copper sulfate solution as the eluent and NaTDC stationary phase, human saliva was analyzed. The chromatogram is shown in FIG. 31. Under the conditions of aqueous cerium chloride solution as the eluent and NaTDC stationary phase, human saliva was analyzed. The chromatogram is shown in FIG. 32. Under the conditions of phosphate buffer as the eluent and CHAPS micellar stationary phase, human saliva was analyzed. The chromatogram is shown in FIG. 33. Particularly the result of FIG. 30 indicates that the indivial compound (α-amylase, tryptophan and another Inorganic ions) were separated well.

② Analysis of Human Urine

Figure 34:
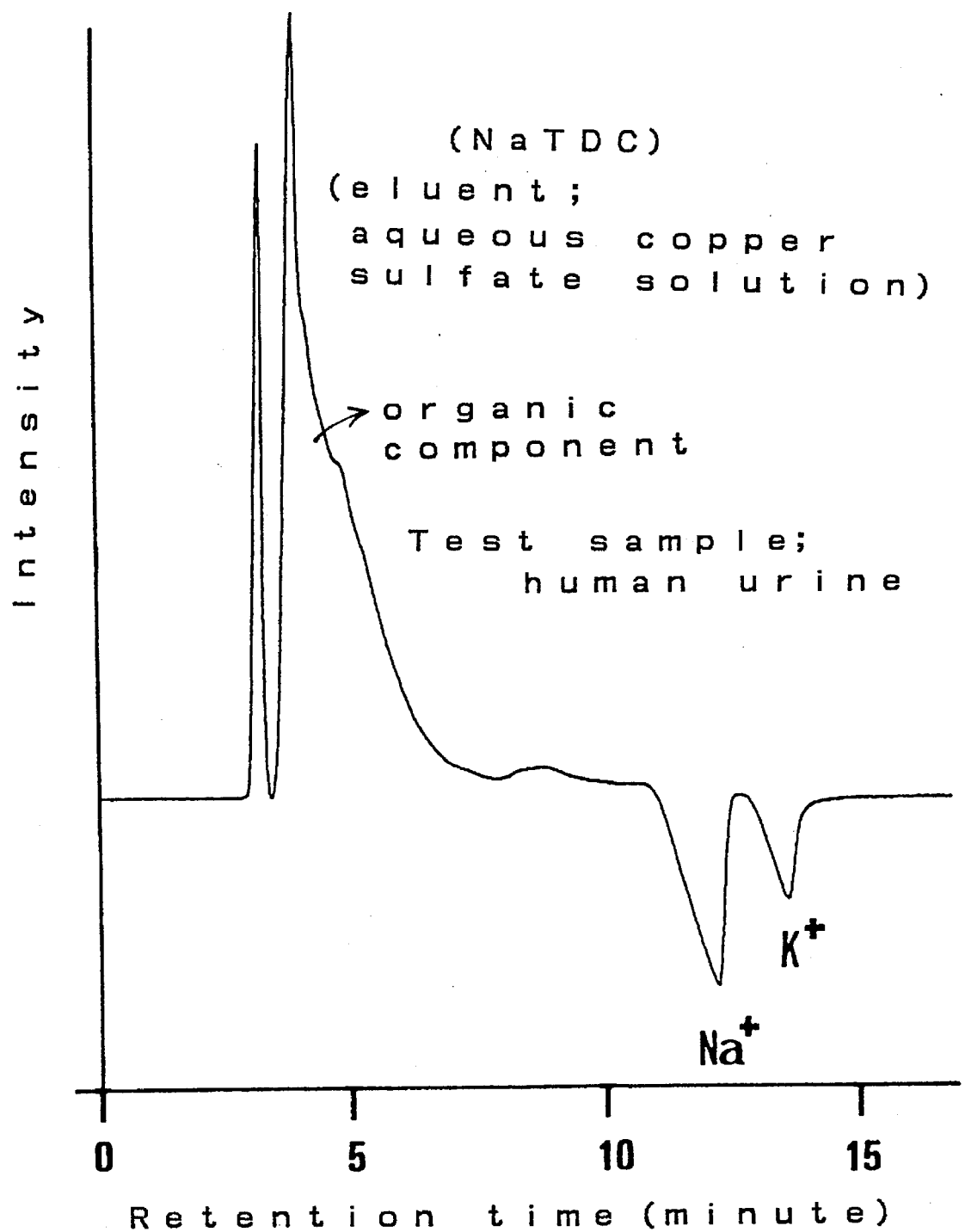
FIG. 34 is an explanatory view depicting the chromatogram from the analysis of human urine, using NaTDC micellar stationary phase and aqueous copper sulfate solution as an eluent in Example.
Figure 35:
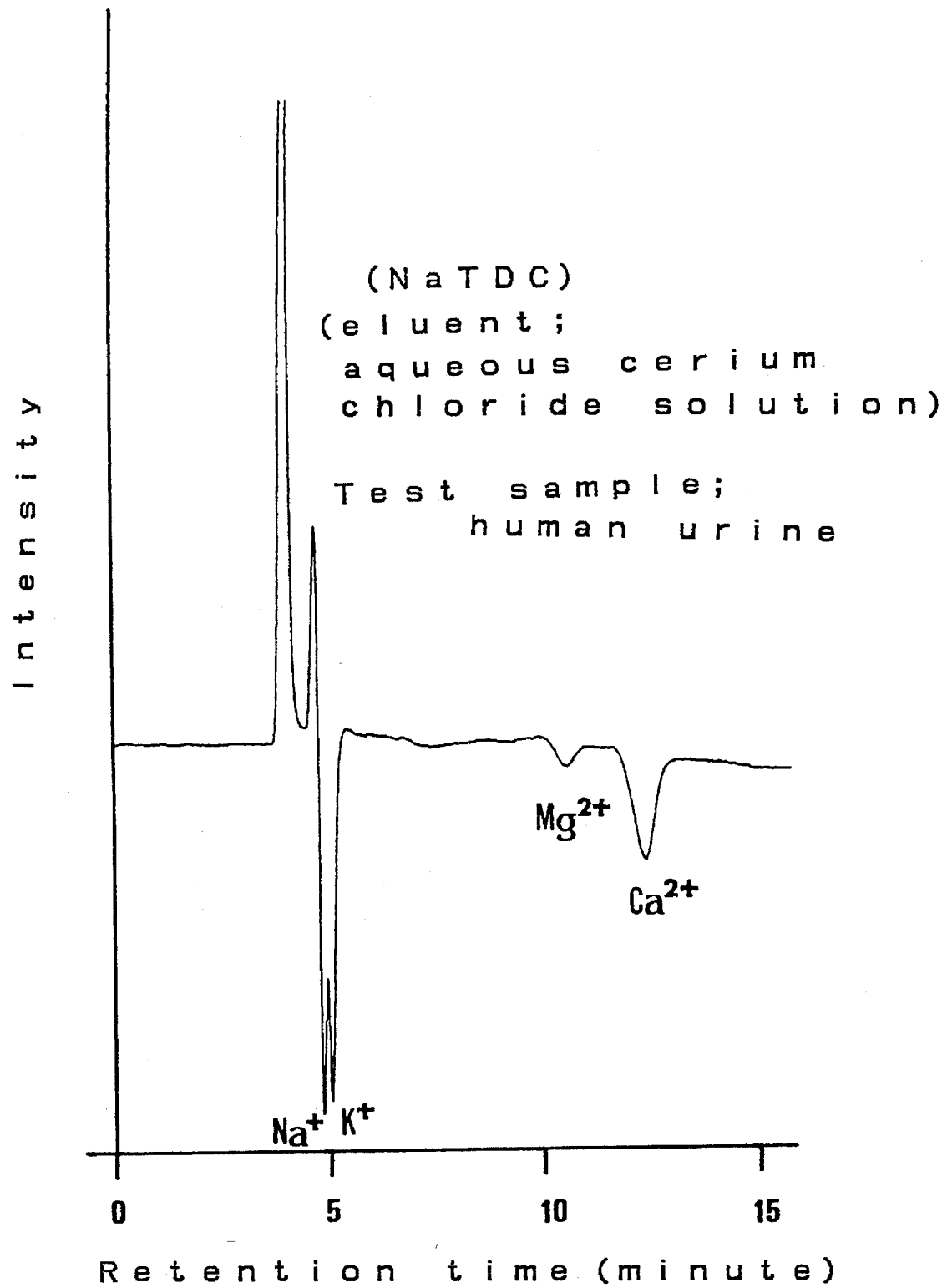
FIG. 35 is an explanatory view depicting the chromatogram from the analysis of human urine, using NaTDC micellar stationary phase and aqueous cerium chloride solution as an eluent in Example.

Under the conditions of aqueous copper sulfate solution as the eluent and NaTDC stationary phase, human urine was analyzed. The chromatogram is shown in FIG. 34. Under the conditions of aqueous cerium chloride solution as the eluent and NaTDC stationary phase, human saliva was analyzed. The chromatogram is shown in FIG. 35. these results indicate that the indivial Inorganic cations were separated.

③ Analysis of Human Serum

Figure 36:
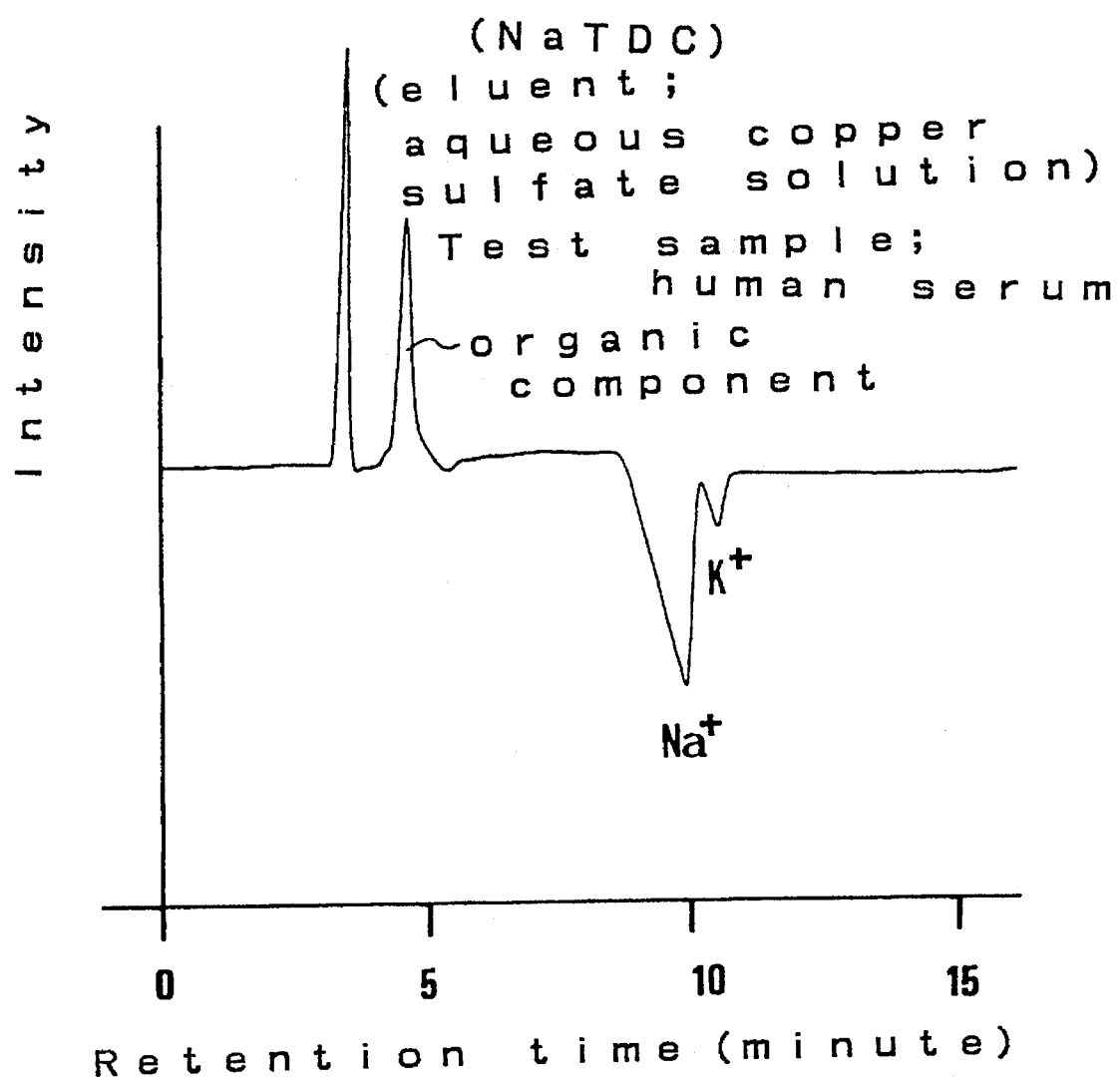
FIG. 36 is an explanatory view depicting the chromatogram from the analysis of human serum, using NaTDC micellar stationary phase and aqueous copper sulfate solution as an eluent in Example.
Figure 37:
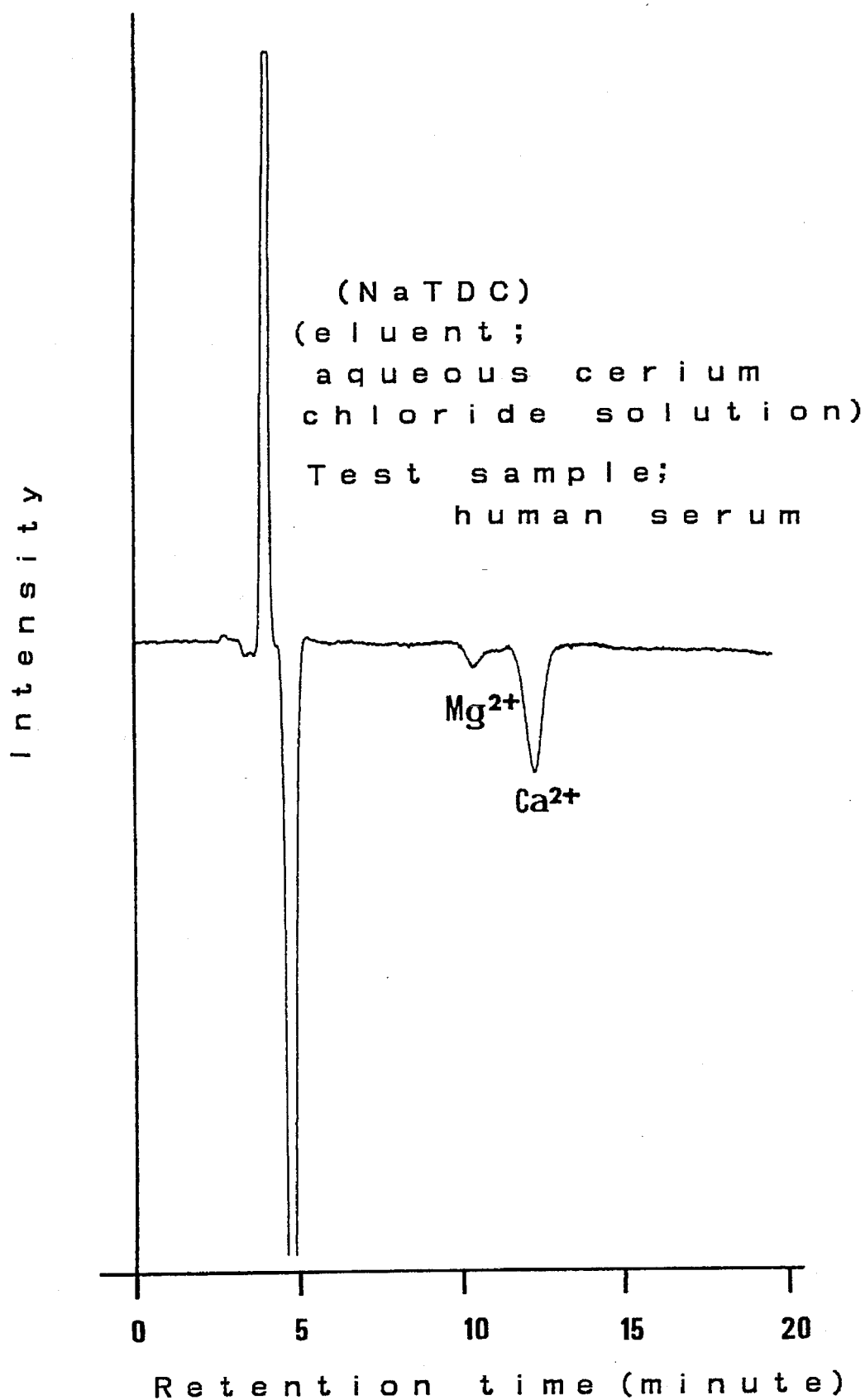
FIG. 37 is an explanatory view depicting the chromatogram from the analysis of human serum, using NaTDC micellar stationary phase and aqueous cerium chloride solution as an eluent in Example.

Under the conditions of aqueous copper sulfate solution as the eluent and NaTDC micellar stationary phase, human serum was analyzed. The chromatogram is shown in FIG. 36. Under the conditions of aqueous cerium chloride solution as the eluent and NaTDC stationary phase, human serum was analyzed. The chromatogram is shown in FIG. 37. these results indicate that predetermined Inorganic cations were separated.

(13) Separation of enantiomers

Figure 38:
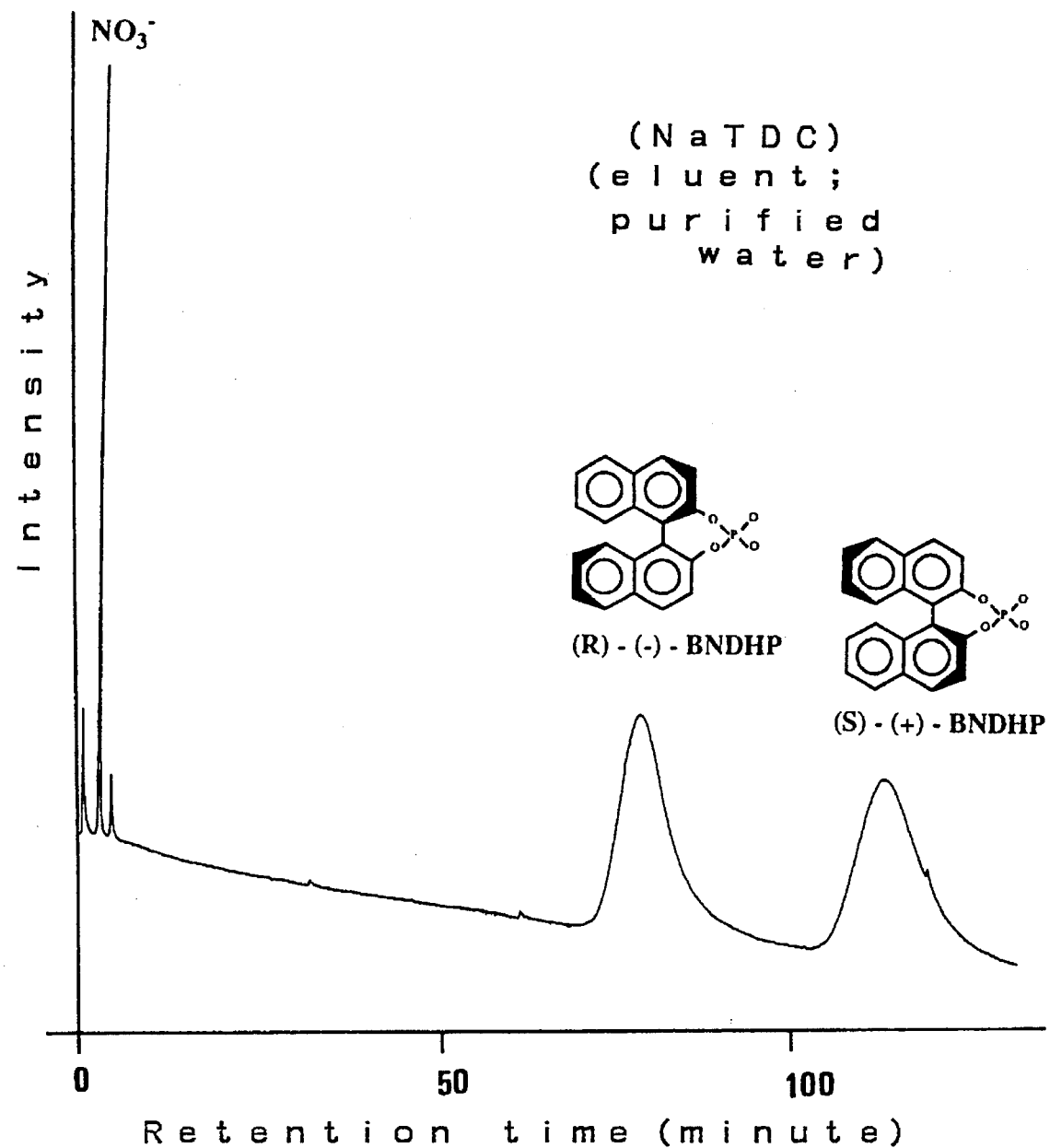
FIG. 38 is an explanatory view depicting the chromatogram from the analysis of enantiomers, using NaTDC micellar stationary phase and pure water as an eluent in Example.

Under the conditions of purified water as the eluent and NaTDC micellar stationary phase, a pair of enantiomers [(R)-(−)-BNDHP and (S)-(+)-BNDHP] shown in FIG. 38 were analyzed. The chromatogram is shown in FIG. 38. The result indicates that indivial enantiomer was separated well. This separation of enantiomers is due to the helical structures of the bile micelles coated on the stationary phase.

The present invention is not limited to the specific examples described above, but may be modified into a variety of examples, depending on the objective and use, within the scope of the present invention.

What is claimed is:

1. A method of separating and analyzing ions by electrostatic ion chromatography, comprising the steps of:

(i) injecting a sample solution containing analyte anions and cations into one end of a separation column packed with a solid phase, and (ii) thereafter eluting the column with water to analyze individually the analyte ions via the difference in the retention time among the individual analyte ions, wherein the solid phase is a zwitterionic stationary phase comprising a support carrier and a zwitterionic layer formed on the surface of the support carrier by directly or indirectly coating thereon 3-[3-cholamidopropyl] dimethyl ammonio]-1-propanesulfonate, 3-[3-cholamidopropyl]dimethyl ammonio]-2-hydroxy-1-propanesulfonate, sodium taurodeoxycholate or sodium taurocholate.

2. The method for separating and analyzing ions by electrostatic ion chromatography as defined in claim 1, wherein the support carrier comprises porous silica gel; a hydrophobic layer generated via an alkylsilane reaction is formed on the surface of the support carrier; and the zwitterionic layer is formed on the surface of the hydrophobic layer.

3. The method as defined in claim 2, wherein the analyte ions comprise tryptophan, anions and cations.

4. The method as defined in claim 2, wherein the analyte ions comprise α-amylase and cations.

5. The method as defined in claim 2, wherein the analyte ions comprise α-amylase and anions.

6. The method as defined in claim 2, wherein the analyte ions comprises α-amylase, tryptophan, anions and cations.

7. A method for separating and analyzing ions by electrostatic ion chromatography as defined in claim 1, wherein a mixture of 3-[3-cholamidopropyl]dimethyl ammonio]-1-propanesulfonate or 3-[3-cholamidopropyl]dimethyl ammonio]-2-hydroxy-1-propanesulfonate and sodium taurodeoxycholate or sodium taurocholate is coated on the surface of the support.

8. The method as defined in claim 1, wherein the analyte ions comprise phenylalanine, 3,4-dihydroxy-phenylalanine and tryptophan.

9. The method as defined in claim 1, wherein the analyte ions comprise α-amylase and cations.

10. The method as defined in claim 1, wherein the analyte ions contain a pair of enantiomers: (R)-(−)-BNDHP and (s)-(−)-BNDHP.

11. A method for separating and analyzing ions by electrostatic ion chromatography as defined in claim 1, wherein the separated analyte ions are detected with a UV detector, an electric conductivity detector or an electrochemical detector.

12. A method for separating and analyzing ions by electrostatic ion chromatography as defined in claim 1, wherein the separated analyte ions are detected with a UV detector, the analyte ions containing UV-non-absorptive components, and the eluent being a solution containing UV-absorptive ions.

* * * * *